US011020091B2

(12) United States Patent
Jin et al.

(10) Patent No.: US 11,020,091 B2
(45) Date of Patent: Jun. 1, 2021

(54) ULTRASOUND IMAGING APPARATUS AND CONTROL METHOD FOR THE SAME

(71) Applicant: SAMSUNG MEDISON CO., LTD., Gangwon-do (KR)

(72) Inventors: Gil-Ju Jin, Seoul (KR); Yuri Kim, Seoul (KR); Mi Jeoung Ahn, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 382 days.

(21) Appl. No.: 15/374,584

(22) Filed: Dec. 9, 2016

(65) Prior Publication Data

US 2018/0021019 A1 Jan. 25, 2018

(30) Foreign Application Priority Data

Jul. 20, 2016 (KR) ........................ 10-2016-0092044

(51) Int. Cl.
*A61B 8/00* (2006.01)
*A61B 8/08* (2006.01)

(52) U.S. Cl.
CPC ............ *A61B 8/469* (2013.01); *A61B 8/4405* (2013.01); *A61B 8/4427* (2013.01);
(Continued)

(58) Field of Classification Search
CPC ....... A61B 8/469; A61B 8/463; A61B 8/5207; A61B 8/467; A61B 8/464; A61B 8/461;
(Continued)

(56) References Cited

U.S. PATENT DOCUMENTS 8,625,882 B2 * 1/2014 Backlund .............. G06F 3/0488 382/154
8,918,146 B2 * 12/2014 Khawand ............ G06F 3/04847 455/411

(Continued)

FOREIGN PATENT DOCUMENTS

EP 2532307 A1 12/2012
EP 2843508 A1 3/2015

(Continued)

OTHER PUBLICATIONS

Extended European Search Report dated Jul. 13, 2017 issued in European Patent Application No. 16207537.8.

(Continued)

*Primary Examiner* — Keith M Raymond
*Assistant Examiner* — Patrick M Mehl
(74) *Attorney, Agent, or Firm* — Morgan, Lewis & Bockius LLP

(57) ABSTRACT

An ultrasound imaging apparatus may control an ultrasound image in various ways and improve user convenience by controlling a touch screen or display output by the ultrasound imaging apparatus in accordance with a touch pressure or touch time of a user.

The ultrasound imaging apparatus may include a probe configured to emit an ultrasonic signal to an object and receive a reflected ultrasonic signal; a processor configured to generate an ultrasound image based on the ultrasonic signal received by the probe; and a touch screen configured to output the ultrasound image generated by the processor and receive a touch of a user or a pressure of the touch, wherein the processor controls the ultrasound image and the touch screen based on the pressure of the touch.

18 Claims, 27 Drawing Sheets

(52) U.S. Cl.
CPC ............ *A61B 8/4472* (2013.01); *A61B 8/461* (2013.01); *A61B 8/463* (2013.01); *A61B 8/464* (2013.01); *A61B 8/465* (2013.01); *A61B 8/466* (2013.01); *A61B 8/467* (2013.01); *A61B 8/5207* (2013.01); *A61B 8/0866* (2013.01); *A61B 8/4477* (2013.01)

(58) Field of Classification Search
CPC ..... A61B 8/466; A61B 8/4472; A61B 8/4427; A61B 8/4405; A61B 8/465; A61B 8/4477; A61B 8/0866; G06F 1/169; G06F 1/1692; G06F 3/0488; G06F 2203/04105
See application file for complete search history.

(56) References Cited

U.S. PATENT DOCUMENTS

2003/0013959 A1 1/2003 Grunwald et al.
2008/0208047 A1* 8/2008 Delso ........................ A61B 8/00 600/437
2009/0131793 A1* 5/2009 Stonefield ................ A61B 8/00 600/443
2009/0256947 A1* 10/2009 Ciurea .................. G06F 3/0488 348/333.12
2010/0004539 A1* 1/2010 Chen .................... A61B 8/0825 600/445
2010/0049046 A1* 2/2010 Peiffer ..................... A61B 8/13 600/443
2011/0113329 A1* 5/2011 Pusateri ................. G16H 40/63 715/702
2012/0105358 A1* 5/2012 Momeyer ........... G06F 3/04883 345/174
2013/0072795 A1* 3/2013 Mo ........................ A61B 8/465 600/443
2014/0050381 A1* 2/2014 Lee ...................... A61B 8/5223 382/131
2014/0063006 A1* 3/2014 Chang ................. G01S 7/52068 345/419
2014/0088428 A1* 3/2014 Yang .................... A61B 8/4444 600/443
2014/0098049 A1* 4/2014 Koch ...................... G06F 3/016 345/173
2014/0187948 A1* 7/2014 Gerard ................ A61B 8/5207 600/443
2014/0276057 A1* 9/2014 Lee ........................ A61B 8/469 600/441
2014/0303501 A1* 10/2014 Jin ......................... A61B 8/463 600/440
2014/0364731 A1* 12/2014 Kann ..................... A61B 8/463 600/440
2015/0138116 A1* 5/2015 Lee ....................... G06F 3/0414 345/173
2015/0209012 A1* 7/2015 Oh ......................... A61B 8/465 600/438
2016/0120508 A1 5/2016 Kim et al.
2016/0125640 A1 5/2016 Lee et al.
2017/0090571 A1* 3/2017 Bjaerum ................. G06F 3/016
2017/0258449 A1* 9/2017 Nielsen ............... G06F 3/04847

FOREIGN PATENT DOCUMENTS

EP 2876604 A1 5/2015
JP 2010-142399 A 7/2010
KR 10-2015-0117120 A 10/2015
WO WO2015136336 A1 * 9/2015 ............. G06F 19/00
WO 2016/083868 A1 6/2016

OTHER PUBLICATIONS

Office Communication from the European Patent Office issued in European Application No. 16 207 537.8 dated Jan. 17, 2019.
European Office Action dated May 28, 2020 issued in European Patent Application No. 16207537.8.

* cited by examiner

ULTRASOUND IMAGING APPARATUS AND CONTROL METHOD FOR THE SAME

CROSS-REFERENCE TO RELATED APPLICATION(S)

This application claims the benefit of Korean Patent Application No. 10-2016-0092044, filed on Jul. 20, 2016 in the Korean Intellectual Property Office, the disclosure of which is incorporated herein by reference.

BACKGROUND

1. Field

Embodiments of the present disclosure relate to ultrasound imaging apparatuses and methods of controlling the same, and more particularly, to ultrasound imaging apparatuses in which an image is displayed on a display or touch screen proportionally to a touch pressure or touch time of a user and methods of controlling the same.

2. Description of the Related Art

Ultrasound imaging apparatuses are used for medical purposes to observe the inside of an object, detect impurities therein, and analyze damages in the object by non-invasively acquiring images of a target region inside the object such as soft tissue tomograms or blood stream tomograms by irradiating ultrasonic signals generated by a transducer of a probe toward the target region from the surface of the object and receiving reflected ultrasonic signals (ultrasonic echo signals).

Since ultrasound imaging apparatuses are smaller and less expensive, display images in real time, and provide high safety without causing X-ray exposure, as compared to other diagnostic imaging apparatuses, such as X-ray diagnosis apparatuses, X-ray computerized tomography scanners, magnetic resonance imaging (MRI) apparatuses, and nuclear medicine diagnosis apparatuses, the ultrasound imaging apparatuses have been widely used together with other diagnostic imaging apparatuses.

Meanwhile, the ultrasound imaging apparatus displays information about the inside of the object using a two-dimensional (2D) or three-dimensional (3D) image to the user by analyzing the received ultrasonic signals. In addition, the ultrasound imaging apparatus assists the user to easily recognize the inside of the object by converting the output image.

In this regard, the ultrasound imaging apparatus may provide various user interfaces (UIs) or user experiences (UXs) to assist the user to more easily recognize the inside of the object. Also, with recent trends of using portable and compact ultrasound imaging apparatuses, developments of UIs and UXs have been highlighted and various research thereinto has been conducted.

SUMMARY

Therefore, it is an aspect of the present disclosure to provide an ultrasound imaging apparatus configured to control an ultrasound image in various ways and improve user convenience by controlling a touch screen or display output by the ultrasound imaging apparatus in accordance with a touch pressure or touch time of a user, and a method of controlling the same.

Additional aspects of the disclosure will be set forth in part in the description which follows and, in part, will be obvious from the description, or may be learned by practice of the disclosure.

In accordance with one aspect of the present disclosure, an ultrasound imaging apparatus includes a probe configured to emit an ultrasonic signal to an object and receive a reflected ultrasonic signal; a processor configured to generate an ultrasound image based on the ultrasonic signal received by the probe; and a touch screen configured to output the ultrasound image generated by the processor and receive a touch of a user or a pressure of the touch, wherein the processor controls the ultrasound image and the touch screen based on the pressure of the touch.

The processor may select a depth of the ultrasound image based on the pressure of the touch.

The processor may remove an image of the object having a predetermined intensity range to the depth based on the pressure of the touch.

The processor may control transparency of the image of the object having a predetermined intensity range to the depth based on the pressure of the touch.

The processor may control focusing of the ultrasound image based on the pressure of the touch.

The processor may control a region of interest in the ultrasound image based on the pressure of the touch.

The processor may control the ultrasound image to rotate based on the pressure of the touch.

The processor may control a menu displayed on the touch screen based on the pressure of the touch.

The touch screen may receive the pressure of the touch via a touch pen.

The processor may control the ultrasound image and the touch screen based on a preset time period during which the pressure is input.

In accordance with another aspect of the present disclosure, a method of controlling an ultrasound imaging apparatus includes emitting an ultrasonic signal to an object and receiving a reflected ultrasonic signal; generating an ultrasound image based on the received ultrasonic signal; receiving a touch of a user and a pressure of the touch after outputting the generated ultrasound image; and controlling the ultrasound image based on the pressure of the touch.

The controlling may include selecting a depth of the ultrasound image based on the pressure of the touch.

The controlling may include removing an image of the object having a predetermined intensity range to the depth based on the pressure of the touch.

The controlling may include controlling transparency of the image of the object having a predetermined intensity range to the depth based on the pressure of the touch.

The controlling may include controlling focusing of the ultrasound image based on the pressure of the touch.

The controlling may include controlling a region of interest in the ultrasound image based on the pressure of the touch.

The controlling may include controlling the ultrasound image to rotate based on the pressure of the touch.

The controlling may include controlling a menu displayed on the touch screen based on the pressure of the touch.

The receiving may include receiving the pressure of the touch via a touch pen.

The controlling may include controlling the ultrasound image based on a preset time period during which the pressure is input.

These and/or other aspects of the disclosure will become apparent and more readily appreciated from the following description of the embodiments, taken in conjunction with the accompanying drawings of which:

DETAILED DESCRIPTION

Figure 1A:
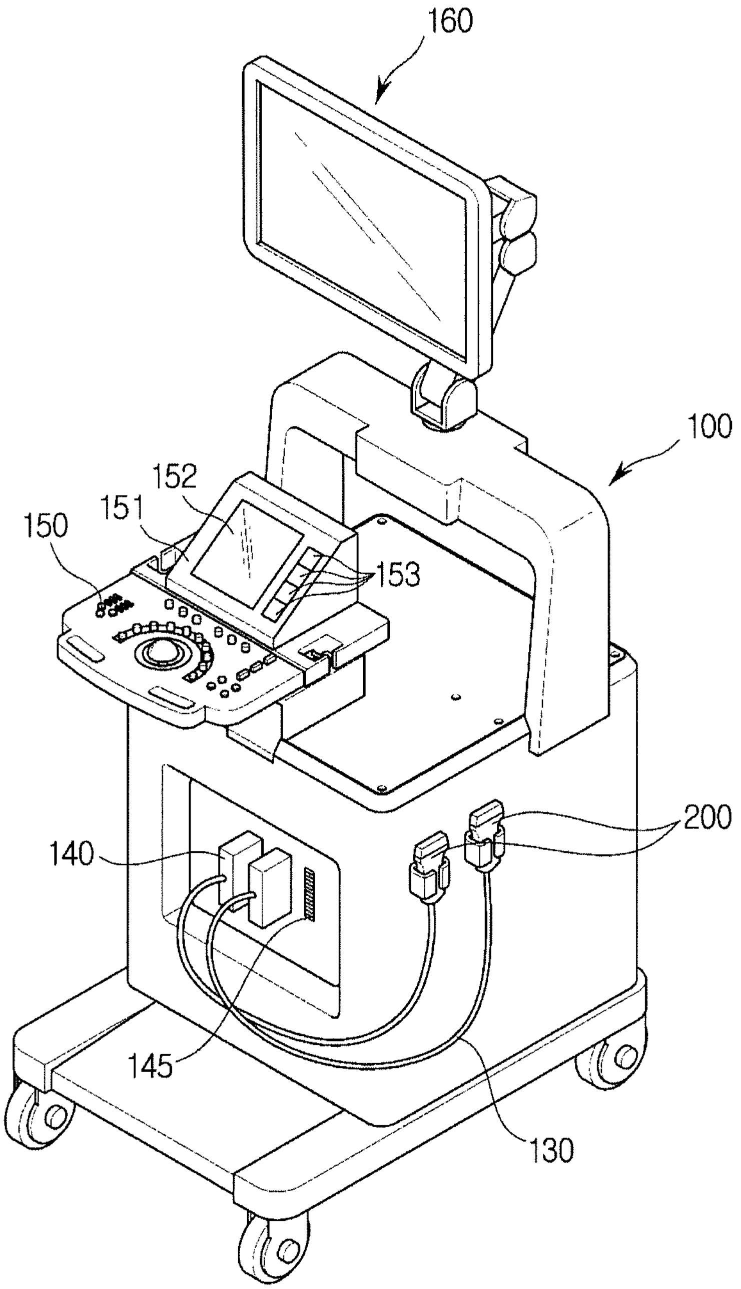
FIG. 1A is a view illustrating an appearance of an ultrasound imaging apparatus according to an embodiment.

Reference will now be made in detail to the embodiments of the present disclosure, examples of which are illustrated in the accompanying drawings, wherein like reference numerals refer to like elements throughout.

The present disclosure may, however, be embodied in many different forms and should not be construed as being limited to the embodiments set forth herein; rather, these embodiments are provided so that this disclosure will be thorough and complete, and will fully convey the concept of the disclosure to those of ordinary skill in the art.

Hereinafter, an ultrasound imaging apparatus and a method of controlling the same according to an embodiment of the present disclosure will be described in detail with reference to the accompanying drawings.

Throughout the specification, the term “object” refers to human or animal or a part of or the entire body of human or animal. For example, the object may include organs such as liver, heart, uterus, brain, breast, and abdomen or blood vessels. Also, as used herein, the term “user” refers to medical professionals such as doctors, nurses, medical laboratory technologists, medical imaging professionals, medical equipment technicians, and the like, without being limited thereto.

As used herein, the term “ultrasound image” refers to not only an image of the object acquired using ultrasound but also an image of the object acquired using an X-ray diagnostic apparatus, a computerized tomography (CT) scanner, a magnetic resonance imaging (MRI) apparatus, and a nuclear medicine diagnosis apparatus.

Throughout the specification, the term “include” an element does not preclude the other elements but further includes an element unless otherwise stated. In addition, the terms “unit” and “module” as used herein, refer to units to perform at least one function or operation, and may be implemented using a software component, a hardware component, or any combination thereof.

Hereinafter, an ultrasound imaging apparatus and a method of controlling the same will be described with reference to the accompanying drawings.

FIG. 1A is a view illustrating an appearance of an ultrasound imaging apparatus according to an embodiment.

Referring to FIG. 1A, an ultrasound imaging apparatus 100 according to an embodiment may include a main body, a display 160 connected to the main body, a control panel 150, an input device 151, and an ultrasound probe 200.

A plurality of casters may be provided at the bottom of the main body to allow the ultrasound imaging apparatus 100 to move. The plurality of casters may fix the ultrasound imaging apparatus 100 to a predetermined position or move the ultrasound imaging apparatus 100 in a predetermined direction. This type of the ultrasound imaging apparatus 100 may be referred to as a cart-type ultrasound imaging apparatus.

Figure 1B:
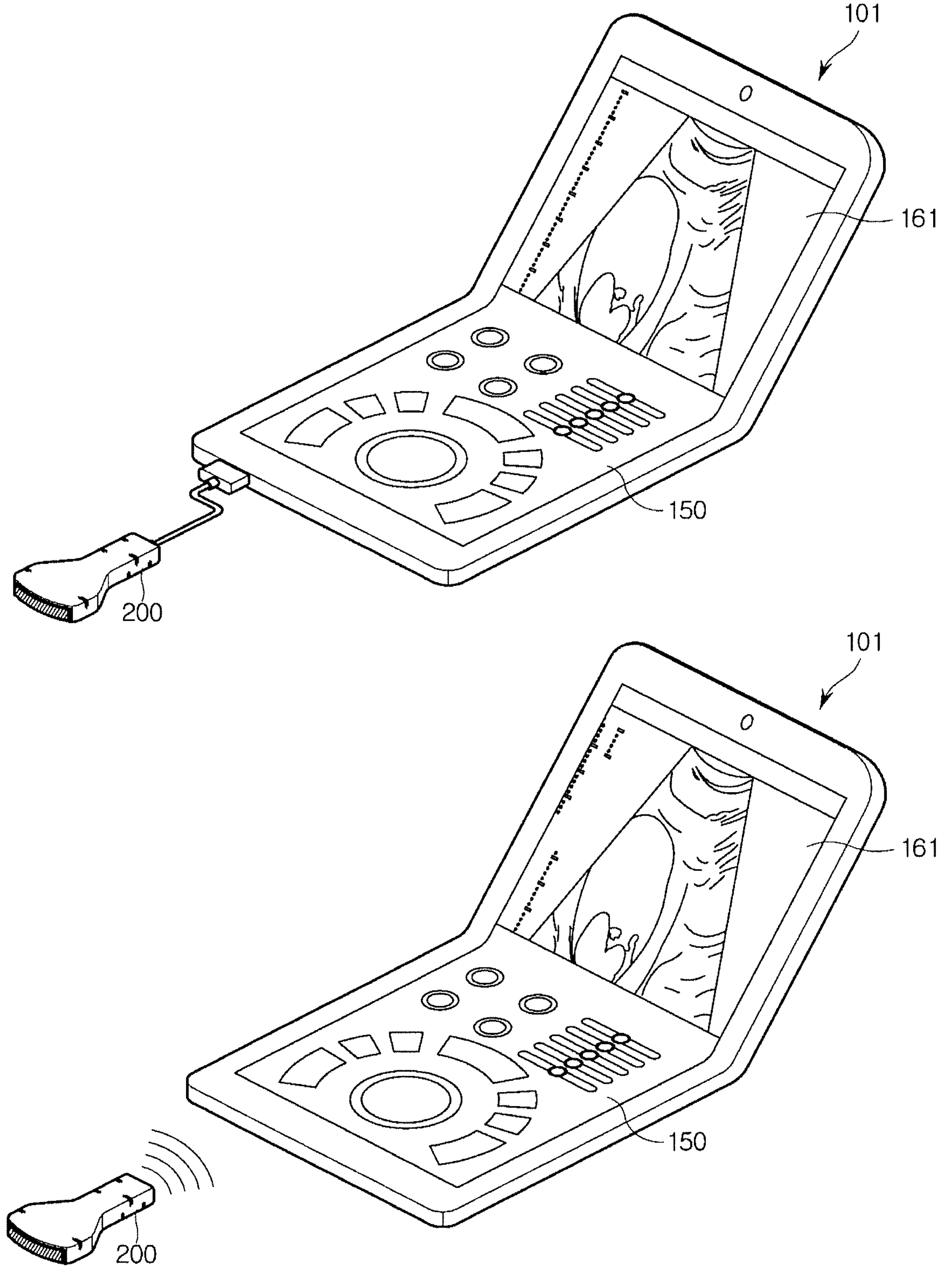
FIG. 1B is a view illustrating an ultrasound imaging apparatus according to another embodiment.

Meanwhile, the ultrasound imaging apparatus 100 according to an embodiment may also be a portable apparatus suitable for long distance travel which is different from that illustrated in FIG. 1A. That is, as illustrated in FIG. 1B, the ultrasound imaging apparatus may not be provided with the casters.

The ultrasound probe 200 may transmit/receive ultrasound to/from an object in contact with the surface of the body of the object. Particularly, the ultrasound probe 200 transmits ultrasound in accordance with an ultrasonic signal, i.e., an electric signal, received from the main body, receives echo ultrasound reflected by a given region inside the object, and transmits an ultrasonic echo signal corresponding thereto to the main body.

The ultrasound probe 200 may be connected to one end of a cable 130, and the other end of the cable 130 may be connected to a male connector 140. The male connector 140 connected to the other end of the cable 130 may be physically coupled to a female connector 145 of the main body.

Although a single ultrasound probe 200 may be connected to the main body, a plurality of ultrasound probes 200 may also be connected to one main body. To this end, a plurality of female connectors may be installed in the main body. Although FIG. 1A illustrates that two ultrasound probes 200 are connected to one main body, the embodiment is not limited thereto.

Meanwhile, the ultrasound probe 200 may also be wirelessly connected to the main body, which is different from FIG. 1A. In this case, the ultrasound probe 200 may transmit the ultrasonic echo signal corresponding to the echo ultrasound received from the object via a wireless communication network.

The ultrasound probe 200 may include a transducer and a multiplexer (MUX) circuit. Meanwhile, an ultrasound probe 200 according to another embodiment may further include a beamforming device in addition to the transducer and the MUX circuit.

The ultrasound imaging apparatus 100 may receive the ultrasonic echo signal from the ultrasound probe 200 and generate an ultrasound image based on the received signal.

The generated ultrasound image may be provided to a user via the display unit 160. The user may visually identify the ultrasound image about the inside of the object received via the display unit 160 and then diagnose the object, i.e., a patient.

The display unit 160 may display various user interfaces (UIs) or user experiences (UXs) related to controlling of the ultrasound imaging apparatus 100.

The user may identify the UI received via the display unit 160 and input a control command about the ultrasound imaging apparatus 100 or a component of the ultrasound imaging apparatus 100 via the control panel 150.

In addition, although the user inputs the control command via the control panel 150 according to the present embodiment, the user may also input by directly touching the display unit 160. This will be described later in more detail.

The display unit 160 may be implemented using any known display such as a cathode ray tube (CRT) and a liquid crystal display (LCD) and may also provide a three-dimensional (3D) image as well as a two-dimensional (2D) image. Also, the display unit 160 includes a touch screen panel, which will be described later, and may further include a light emitting diode (LED) panel or an organic light emitting diode (OLED) panel.

The control panel 150 may be configured to receive a command related to operation of the ultrasound imaging apparatus 100. The user may input commands to start a diagnosis, select a target region to be diagnosed, select a diagnosis type, select a mode to output a final ultrasound image, and the like, via the control panel 150.

For example, the control panel 150 may be disposed on the main body as illustrated in FIG. 1A. In this case, the control panel 150 may include at least one of a switch, a key, a wheel, a joystick, a trackball, and a knob.

The control panel 150 of the ultrasound imaging apparatus 100 according to an embodiment may further include the input device 151. Particularly, the input device 151 may include a touch screen 152 and a mechanical input unit 153, and the user may input the control command to control the ultrasound image output from the ultrasound imaging apparatus 100 via the touch screen 152 or the mechanical input unit 153.

The input unit 153 that is a mechanical input unit may be a general button type input unit pressed for an input or a rotating input unit.

The touch screen 152 may be an input unit to receive a control command to control the ultrasound image or other control commands from the user by touching.

Particularly, the touch screen 152 may be implemented using a touch screen panel (TSP), and the TSP refers to an input device configured to recognize a position of a touch of the user or a pressure applied thereto when a finger of the user or a touch pen 155 (FIG. 2B) presses or contacts a screen.

The touch screen 152 according to an embodiment may receive the position of the finger of the user or the touch pen 155 and the pressure applied thereto, and the ultrasound imaging apparatus 100 may control the ultrasound image based on a touch pressure or touch time input therethrough.

The touch screen 152 may also receive information about controlling of the ultrasound imaging apparatus 100 in addition to receiving a command to control the ultrasound image. For example, the touch screen 152 may receive information about a menu or guidelines based on the pressure input by the user while displaying the menu or guidelines required for setting of the ultrasound imaging apparatus 100.

Also, the touch screen 152 may display a menu or guidelines required for next settings as a UI while outputting an ultrasound image converted based on the pressure of the user again. That is, the touch screen 152 may serve as an input unit to receive a touch input of the user simultaneously as an output unit to display the ultrasound image.

Figure 4A:
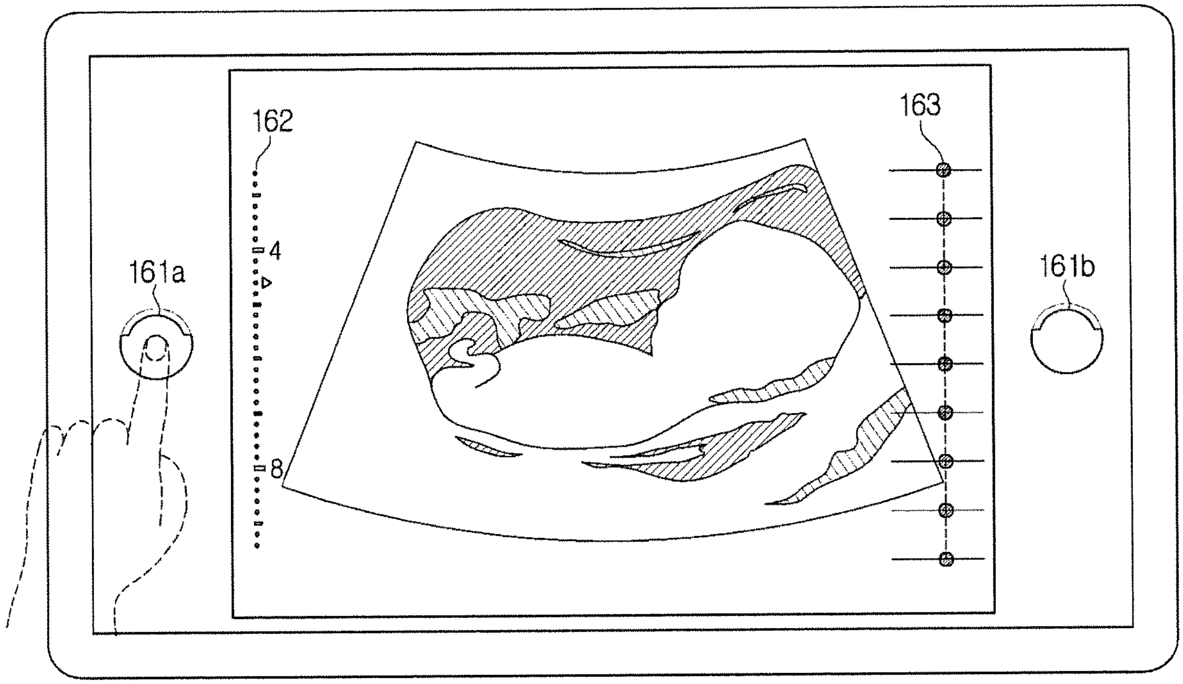
FIGS. 4A to 4D illustrate examples of operation in which screens are changed in accordance with touch pressure or touch time applied to the touch screen.

Various embodiments about screens displayed on the touch screen 152 and control operation of the ultrasound imaging apparatus 100 will be described later in detail with reference to FIG. 4A.

The touch screen 152 may be implemented using a LCD panel, a LED panel, an OLED panel, or the like, without being limited thereto.

Meanwhile, the input device 151 including the touch screen 152 is distinguished from the display unit 160 outputting the ultrasound image in FIG. 1A, a portable ultrasound imaging apparatus 101 may display both input buttons and output images on a single TSP.

FIG. 1B is a view illustrating an ultrasound imaging apparatus according to another embodiment. In this regard, descriptions presented above with reference to FIG. 1A will not be repeated herein.

The ultrasound imaging apparatus 100 according to another embodiment may be a portable ultrasound imaging apparatus 101 that is smaller than the cart-type ultrasound imaging apparatus illustrated in FIG. 1A.

Referring to FIG. 1B, the portable ultrasound imaging apparatus 101 may include the control panel 150 and a flexible display 161 having touch screen functions.

In addition, as described above with reference to FIG. 1A, the portable ultrasound imaging apparatus 101 may be connected to the ultrasound probe 200 via a wired or wireless communication network. If wirelessly connected, the ultrasound probe 200 may transmit the ultrasonic echo signal corresponding to the echo ultrasound received from the object to the main body of the portable ultrasound imaging apparatus 101 via a wireless communication network.

The control panel 150 may receive an input command to control the ultrasound image from the user as described above with reference to FIG. 1A. However, the control panel 150 of the portable ultrasound imaging apparatus 101 may include smaller buttons than those of the control panel 150 of the ultrasound imaging apparatus 100 illustrated in FIG. 1A.

The portable ultrasound imaging apparatus 101 may include the flexible display 161. Here, the flexible display 161, which is a display manufactured using a flexible material such as a plastic substrate, is lighter and less fragile than other displays and is folded, rolled, or bent due to flexibility of the material.

The flexible display 161 may receive a touch of the user or a pressure of the touch simultaneously outputting the ultrasound image of the object. In addition, the flexible display 161 may change or control the output ultrasound image proportionally to a touch pressure or touch time of the user. This will be described later in more detail.

Meanwhile, the portable ultrasound imaging apparatus 101 illustrated in FIG. 1B is an example of the portable device, without being limited thereto. That is, the portable ultrasound imaging apparatus 101 may also be a picture archiving and communication system (PACS) viewer, a smart phone, a laptop computer, a personal digital assistant (PDA), and a tablet PC, without being limited thereto.

Figure 2A:
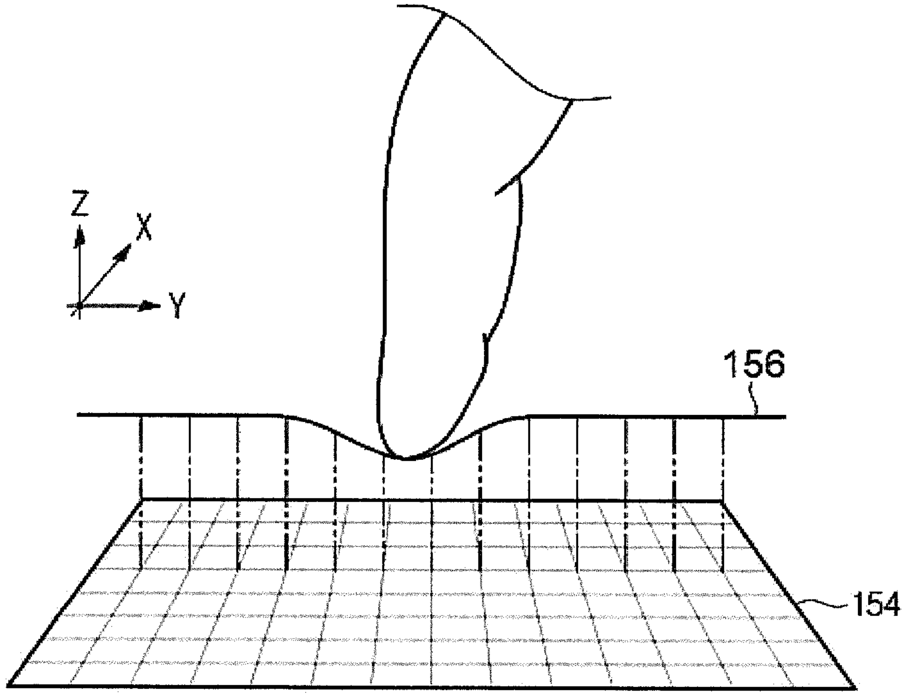
FIG. 2A is a view for describing Force Touch performed on a touch panel.
Figure 2B:
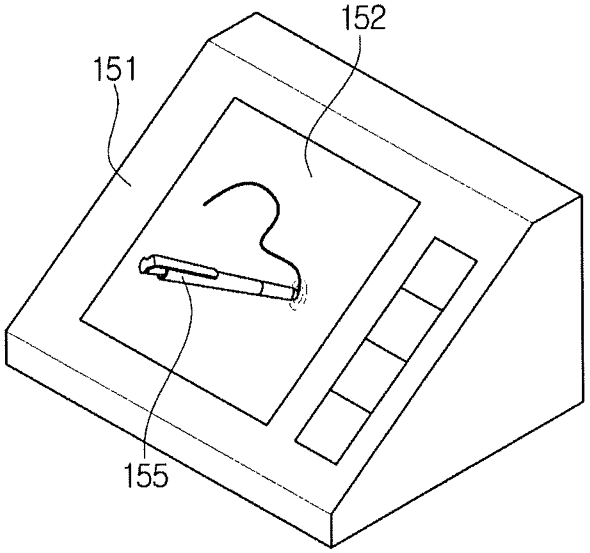
FIG. 2B is a view for describing a touch of a touch pen.

FIGS. 2A and 2B are views for describing a touch panel of a display.

Particularly, FIG. 2A is a view for describing Force Touch performed on a touch panel. FIG. 2B is a view for describing a touch of a touch pen.

As described above, the touch screen panel (TSP) refers to a system configured to recognize a position of a finger of a user or a pen when the finger or the pen presses or contacts the TSP.

The TSP may include a touch panel, a controller integrated circuit (IC), a driver software (SW), and the like. The touch panel includes an upper panel deposited with a transparent electrode (indium tin oxide (ITO)) and a lower panel (film or glass). In response to a contact with the transparent electrode, the touch panel recognizes a position of a signal generated by a change in electric capacity. Then, the touch panel transmits information about the position of the signal to the controller IC.

The controller IC converts an analog signal received from the transparent electrode into a digital signal to represent the position as coordinates displayed on the screen.

The driver SW is a program configured to receive the digital signal from the controller IC and control the touch panel to operate in accordance with respective operating systems.

Meanwhile, TSPs may be classified into a resistive, a capacitive, an ultrasonic, an infrared, an optical type, and the like according to technology applied thereto.

The touch screen 152 may perform Force Touch to further recognize pressure of the touch as well as recognizing the touch and the position of the touch described above.

Force Touch may include a capacitive touch sensor integrated into a backlight 154 located below an upper film 156 of the touch screen 152 as illustrated in FIG. 2A as a hardware component. When the user touches the touch screen 152 with a pressure, the capacitive touch sensor measures a microscopic change in distance between the upper film 156 and the backlight 154.

As illustrated in FIG. 2A, when a finger of the user presses the touch screen 152, a microscopic change in distance has acceleration in accordance with pressure. The capacitive touch sensor measures a velocity of the microscopic change in distance, thereby measuring pressure using the same.

Force Touch recognizes a 3D direction to recognize a pressure by software. In conventional TSPs by which pressure is not measured, the touch screen 152 recognizes a position of a touch, i.e., information about a 2D position defined by X- and Y-axes. However, Force Touch further recognizes information about a Z-axis that is a direction of a force pressed by the user.

That is, Force Touch converts information about the touch position by the user on the touch screen 152 and the pressure applied thereto into 3D Z-axial coordinate information and controls the driver SW to execute a program in accordance with information about the coordinate.

As described above, FIG. 2B is a view for describing an example of inputting a control command to the touch screen 152 of the ultrasound imaging apparatus 100 using a touch pen 155 by the user.

Particularly, the touch pen 155 that inputs a touch and a pressure to the touch screen 152 of the ultrasound imaging apparatus 100 illustrated in FIG. 2B may be a stylus pen.

The stylus pen, as one example of the touch pen 155, is an electronic pen and is used together with the touch screen 152 or an exclusive flat panel sensor. The stylus pens may be classified into pressure-sensitive, capacitive, and electromagnetic induction types in accordance with methods of sensing signals.

For example, the capacitive stylus pen refers to a stylus pen recognizing a touch and a touch pressure by using a change in electric signals. Thus, a conductor is mounted on a contact portion of the capacitive stylus pen.

When the conductor of the stylus pen contacts a magnetic field formed on the film of the touch screen 152, a current is generated by electromagnetic induction, and the stylus pen operates without having a battery.

Meanwhile, although the stylus pen is described as an example of the touch pen 155 according to an embodiment, any other touch pens and devices may also be used to sense the pressure of the touch, without being limited thereto.

In addition to the methods of recognizing Force Touch described above with reference to FIGS. 2A and 2B, the embodiment may also include any other methods used to recognize the touch pressure by the user, without being limited thereto.

Figure 3A:
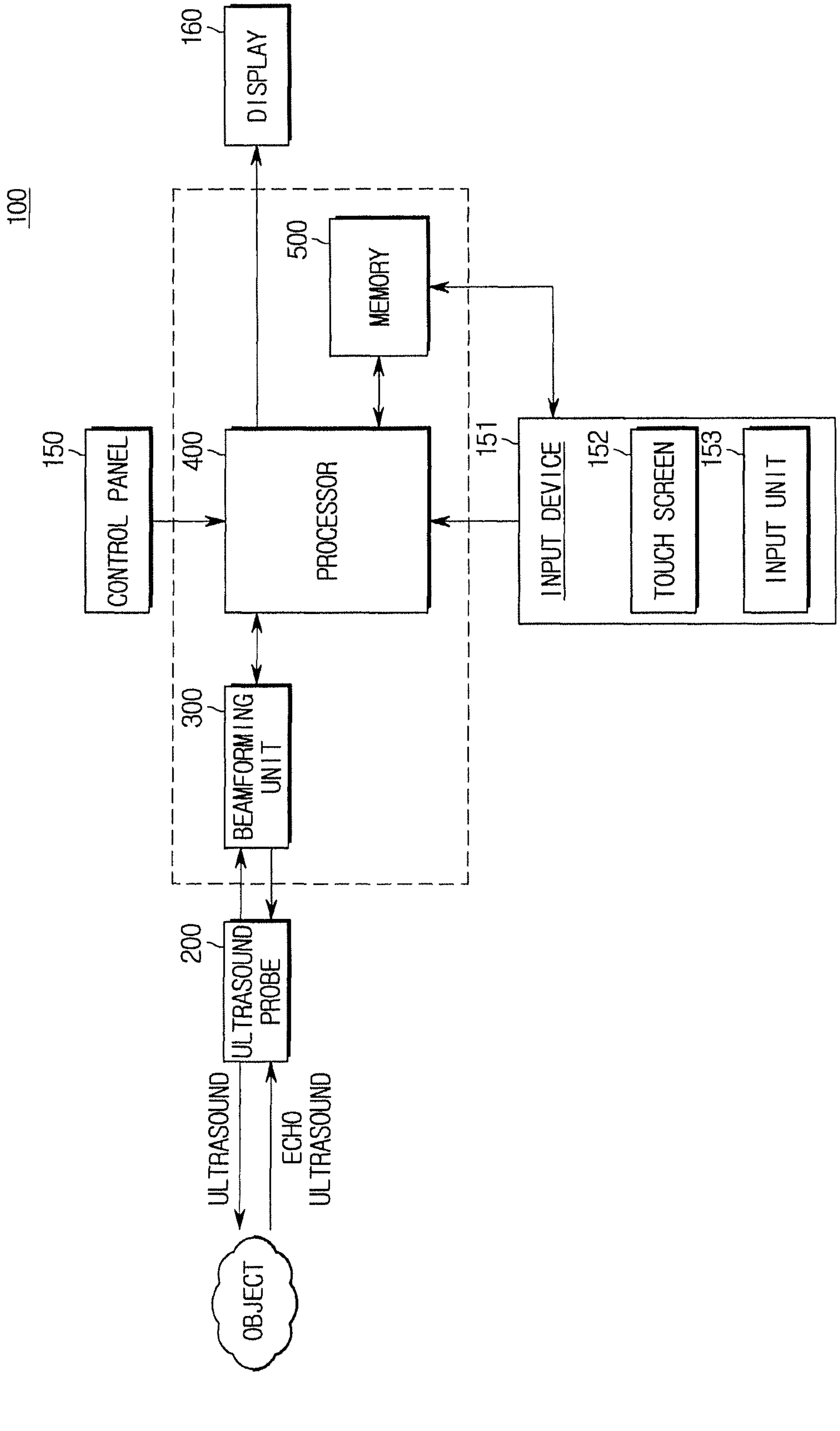
FIG. 3A is a control block diagram illustrating an ultrasound imaging apparatus according to an embodiment.

FIG. 3A is a control block diagram illustrating an ultrasound imaging apparatus according to an embodiment.

Referring to FIG. 3A, the ultrasound imaging apparatus 100 according to an embodiment may include the ultrasound probe 200, a beamforming unit 300, a processor 400, and a memory 500.

The ultrasound probe 200 may be implemented in various manners within technical concepts to acquire images of the object.

As described above, the ultrasound probe 200 that contacts the surface of the body of the object may transmit/receive ultrasound to/from the object. Particularly, the ultrasound probe 200 generates ultrasound in accordance with input pulses, transmits the ultrasound into the object, and receives echo ultrasound reflected by a given region inside the object.

The beamforming unit 300 may perform beamforming such that ultrasound transmitted from and received by the ultrasound probe 200 is focused. The beamforming unit 300 includes a transmit beam former (not shown) and a receive beam former (not shown) to perform interconversion between analog signals and digital signals and control time difference of ultrasound transmitted from or received by one or more transducers.

Although the beamforming unit 300 may be included in the main body of the ultrasound imaging apparatus as illustrated in FIG. 3A, the ultrasound probe 200 may also include the beamforming unit 300. The ultrasound probe 200 including the beamforming unit 300 will be described later with reference to FIG. 3B. The processor 400 controls the overall operation of the ultrasound imaging apparatus 100.

First, the processor 400 may store information received from the control panel 150 or the input device 151 in the memory 500. That is, when the user applies a pressure to the touch screen 152 of the input device 151, the processor 400 may perform an UI operation preset in the memory 500 in accordance with the pressure. This will be described later in more detail with reference to FIG. 4A.

The processor 400 may generate and process an ultrasound image by processing ultrasonic echo signals beamformed by the beamforming unit 300.

For example, the processor 400 may apply time gain compensation (TGC) to the beamformed ultrasonic echo signal. Then, the processor 400 may set a dynamic range (DR). After setting the DR, the processor 400 may compress the ultrasonic echo signal of the set DR. Finally, the processor 400 may rectify the ultrasonic echo signal and remove noise therefrom.

The processor 400 may generate various types of ultrasound images. Examples of the ultrasound images generated by the processor 400 may include an amplitude mode (A-mode) image, a brightness mode (B-mode) image, a motion mode (M-mode) image, and a Doppler mode image.

The processor 400 according to an embodiment may repeat generating and changing of an image in accordance with the touch pressure or touch time of the user and may also display an image including a predetermined UI on the display 160 or the touch screen 152.

Meanwhile, the processor 400 may include a single or a plurality of processors. The processor 400 may be implemented using an array of a plurality of logic gates or a combination of a universal micro-processor and a memory storing a program executable by the micro-processor. For example, the processor 400 may be implemented using a universal CPU.

The memory 500 stores various data and UI graphics required in the ultrasound imaging apparatus 100. Also, the memory 500 may be disposed outside the ultrasound imaging apparatus 100 and transmit/receive data to/from the ultrasound imaging apparatus 100 via a wired or wireless communication network.

The memory 500 may include high-speed random access memory, magnetic disk, static random access memory (SRAM), dynamic random access memory (DRAM), read-only memory (ROM), and the like.

Also, the memory 500 may be detachable from the ultrasound imaging apparatus 100. That is, the memory 500 may include a compact flash (CF) card, a smart media (SD) card, a smart media (SM) card, a multimedia card (MMC), and a memory stick, without being limited thereto.

The control panel 150 may input a control command to control the ultrasound imaging apparatus or a component of the ultrasound imaging apparatus as described above with reference to FIG. 1. Descriptions presented above will not be repeated.

The input device 151 may include the touch screen 152 and the mechanical input unit 153. Data and UI graphics stored in the memory 500 are displayed through the touch screen 152 and the touch of the user and the pressure of the touch may also be received therethrough.

The mechanical input unit 153 receives an input from the user, converts the input into an electric signal, and transmits the converted signal to the processor 400. Since the input device 151 is described above with reference to FIG. 1A, descriptions thereof will not be given.

The display unit 160 may display various UIs related to controlling of the ultrasound imaging apparatus 100 and display ultrasound images acquired during ultrasound diagnosis.

Also, the display unit 160 may provide a 2D or 3D image related to the ultrasound image and receive the touch of the user and the pressure of the touch replacing functions of the input device 151.

In the ultrasound imaging apparatuses 100 illustrated in FIGS. 1A and 3A, the display 160 is distinguished from the touch screen 152. However, the display 160 and the touch screen 152 may be integrated in the ultrasound imaging apparatus 100 according to an embodiment to display the ultrasound image and the UI button and serve as the input device to recognize the touch of the user.

Figure 3B:
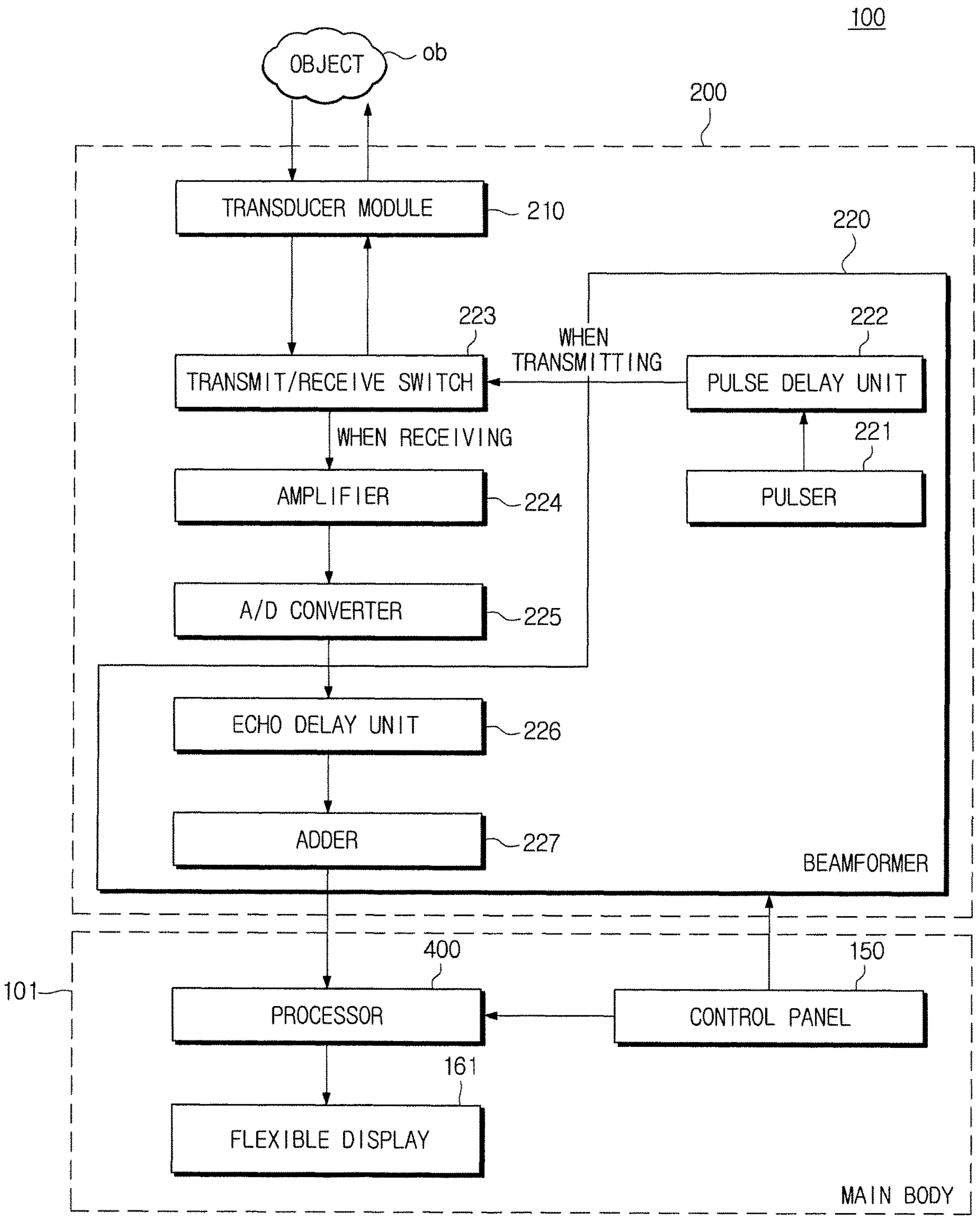
FIG. 3B is a control block diagram of a portable ultrasound imaging apparatus according to another embodiment.

FIG. 3B is a control block diagram of a portable ultrasound imaging apparatus according to another embodiment.

In the portable ultrasound imaging apparatus 101 according to an embodiment, a probe 200 may include a beamforming device to reduce the size of the main body.

Referring to FIG. 3B, the probe 200 may include a transducer module 210, a beam former 220, a transmit/receive switch 223, an amplifier 224, and an analog-to-digital converter (A/D converter) 225.

The transducer module 210 generates ultrasound in accordance with a pulse signal and emits the ultrasound toward the object ob. The ultrasound emitted to the object ob is reflected by a target region inside the object ob. The transducer module 210 receives reflected echo ultrasound and converts the received echo ultrasound into an electric signal.

The beam former 220 may appropriately apply time delays to the emitted ultrasound or received echo ultrasound to simultaneously focus the ultrasound generated by the transducer module 210 on one target region of the object ob at a desired time or remove time difference of arrival at respective transducer elements included in the transducer module 210 among the echo ultrasound reflected by the target region of the object ob as described above with reference to FIG. 3A.

Particularly, the beam former 220 may include a pulser 221, a pulse delay unit 222, an echo delay unit 226, and an adder 227.

The pulser 221 generates AC voltage (i.e., pulse) to drive the transducer module 210 while emitting ultrasound.

The number of the pulsers 221 corresponds to the number of the transducer elements included in the transducer module 210 or the number of channels.

While emitting ultrasound, the transmit/receive switch 223 may operate in a transmit mode, and the pulser 221 may generate a voltage pulse in the range of, for example, about −80 V to about +80 V or about 0 V to about 200 V as a transmit pulse and input the generated voltage pulse to each of the transducer elements of the transducer module 210.

The pulse delay unit 222 may apply a delay time to the pulse in accordance with a focus point and a steering angle of ultrasound to form a transmit signal pattern while emitting ultrasound.

The number of the pulse delay units 222 may also correspond to the number of the transducer elements included in the transducer module 210 or the number of channels.

The pulse delay unit 222 applies time delays to the respective transducer elements such that pulses generated by the respective pulsers 221 to arrive at the focus point. In this case, there may be a plurality of focus points, and the plurality of focus points may constitute one scan line. The time delayed voltage pulses may be input to the respective transducer elements constituting the transducer module 210 as transmit pulses.

The echo delay unit 226 may apply time delays to digital signals of the respective transducer elements in accordance with the focus point and the steering angle while receiving ultrasound.

When the transmit/receive switch 223 operates in a receive mode and the transducer module 210 receives echo ultrasound after emitting ultrasound, the echo delay unit 226 receives digital signals corresponding to the echo ultrasound from the A/D converter 225 and applies time delays to the digital signals of the respective transducer elements included in the transducer module 210 based on the focus point and the steering angle of ultrasound with respect to the target region.

For example, the echo delay unit 226 may be flexibly set delay frequencies based on at least one of parameters including whether a 2D transducer array is included, depth of focus, steering angle, an aperture size, the number of activated transducer elements, and the like and apply delay times to digital signals of the respective transducer elements included in the transducer module 210 in accordance with the set delay frequencies.

The adder 227 adds time-delayed digital signals of the respective transducer elements while receiving ultrasound.

The adder 227 adds digital signals of the respective transducer elements included in the transducer module 210 to which time delays are applied by the echo delay unit 226 to focus thereinto a single digital signal. The focused digital signal is output from the probe 200 and transmitted to the processor 400 of the main body of the portable ultrasound imaging apparatus 101, and the processor 400 performs various image processing to create an ultrasound image after signal processing.

The transmit/receive switch 223 operates in the transmit mode while emitting ultrasound and in the receive mode while receiving ultrasound in accordance with a control signal of the processor 400.

The amplifier 224 amplifies a voltage in accordance with a current output from the transducer module 210.

The amplifier 224 may include a pre-amplifier configured to amplify micro analog signals and a low noise amplifier (LNA) may be used as the pre-amplifier.

In addition, the amplifier 224 may include a variable gain amplifier (VGA, not shown) configured to control a gain value in accordance with an input signal. In this case, the variable gain amplifier may use Time Gain Compensation (TGC) to compensate gains in accordance with the focus point or a distance from the focus point or Lateral Gain Compensation (LGC) to compensate gains in a lateral direction, without being limited thereto.

The A/D converter 225 converts an analog voltage output from the amplifier 224 into a digital signal.

A digital signal converted by the A/D converter 225 is input to the echo delay unit 226 of the beam former 220 in FIG. 3B. However, on the contrary, an analog signal time-delayed by the echo delay unit 226 may also be input to the A/D converter 225. The order is not limited.

The main body of the portable ultrasound imaging apparatus 101 may include a processor 400, a flexible display 161, and a control panel 150.

The processor 400 controls the overall operation of the portable ultrasound imaging apparatus 101 as described above with reference to FIG. 3A. In addition, the processor 400 processes an electric signal received from the probe 200, generates an image, and transmits the generated image to the flexible display 161.

Also, the processor 400 may receive a control command from the control panel 150 and generate or change an ultrasound image depending on intention of the user.

Descriptions about the control panel 150 and the processor 400 presented above with reference to FIG. 3A will not be repeated herein.

Meanwhile, the flexible display 161 may output the image generated by the processor 400 and receive a touch input of the user. The flexible display 161 may transmit the received touch input to the processor 400.

The flexible display 161 of the portable ultrasound imaging apparatus 101 according to an embodiment receives not only the touch input of the user but also an amount of touch pressure or touch time separately.

As described above, the processor 400 provides the user with the user output based on the touch pressure or touch time of the user or various UIs by controlling functions. Examples of the various UIs executed by the portable ultrasound imaging apparatus 101 will be described later in more detail with reference to FIG. 4A and the following drawings.

Meanwhile, the ultrasound imaging apparatus 100 may also include various modified examples in addition to the cart-type or portable ultrasound imaging apparatus as described above, and components included in each imaging apparatus are not limited.

FIGS. 4A to 4D illustrate examples of operation in which screens are changed in accordance with touch pressure or touch time applied to the touch screen. Hereinafter, the drawings will be synthetically described to avoid repeated descriptions.

FIGS. 4A to 4D illustrate output images and UI buttons displayed on the touch screens of the ultrasound imaging apparatus 100.

Particularly, FIGS. 4A to 4D schematically illustrate ultrasound images of a fetus. In addition, the ultrasound imaging apparatus 100 according to an embodiment may output the ultrasound image and a button-shaped UI at a position where the user may touch. Hereinafter, a left button UI is referred to as a first button 161*a*, and a right button UI is referred to as a second button 161*b*.

Meanwhile, the ultrasound imaging apparatus 100 may output values indicating depth and focusing (TGC) as a graph together with the ultrasound image of the object.

As described above, the depth refers to a position of the object at which the ultrasonic signals emitted from the transducers of the ultrasound probe 200 arrive.

TGC refers to a function of amplifying the ultrasonic signals by attenuated degrees according to the depth of the object in order to display echo signals reflected by different positions in the object with the same brightness.

Particularly, the ultrasound emitted from the ultrasound probe 200 attenuates depending on depth while passing through the object. Thus, an intensity of a signal reflected by a closer position of the object to the probe 200 is different from that reflected by a farther position of the object from the probe 200. Thus, the signal reflected by the farther position is output darker. When gain is increased to remove this difference, the closer position is output lighter and the farther position is output darker. Thus, TGC may enable the user to view a region of interest in the object more clearly by controlling the degree of amplification in accordance with depth.

Referring back to FIG. 4A, an axis 162 of a first graph on the left side indicates positions of the object with respect to depth in numeric values and an axis 163 of a second graph on the right side indicates degrees of focusing with respect to TGC in numeric values.

The user may touch the first button 161*a* to adjust the depth.

When the user touches the first button 161*a*, the processor 400 may display a cursor having a triangular shape to display a depth at a predetermined position.

Figure 4B:
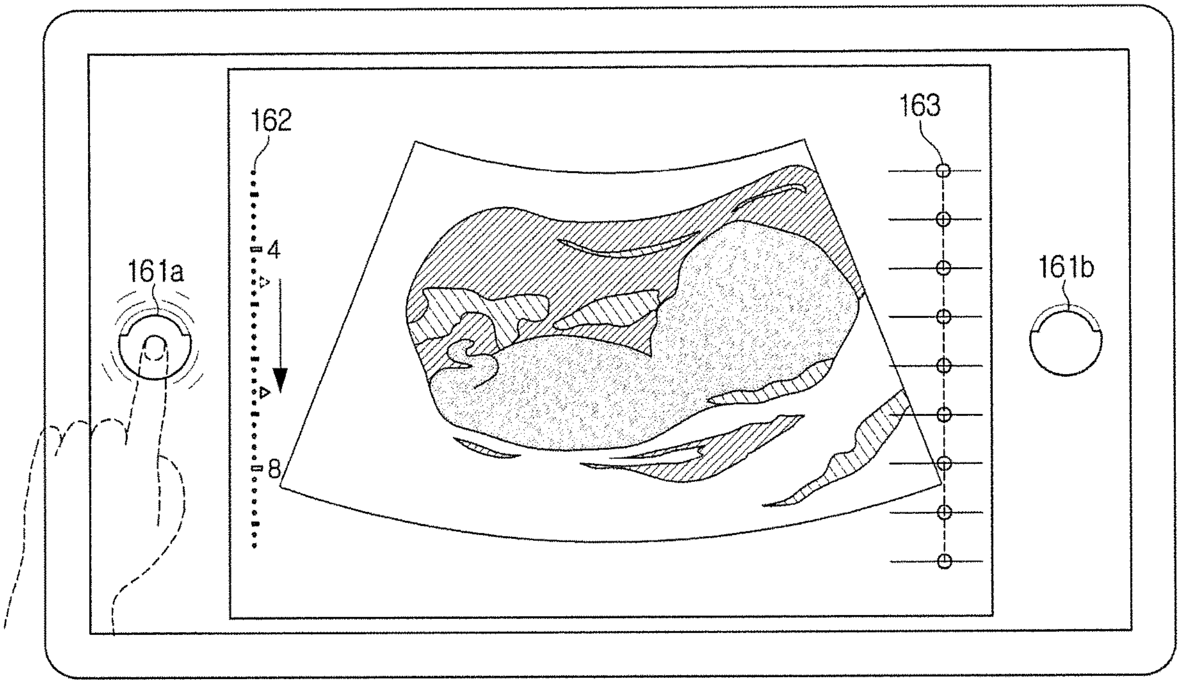

Then, the user may press the first button 161*a* of the touch screen 152 with a greater pressure. In FIG. 4B, waves around the first button 161*a* indicate an operation of applying pressure by the user.

When the user applies a pressure to the first button 161*a* of the touch screen as illustrated in FIG. 4B, the processor 400 controls the cursor having the triangular shape and indicating depth toward the axis 162 of the first graph based on the amount of the pressure and touch time. When the cursor arrives at a desired position, the user may detach from the finger from the touch screen 152 to stop inputting a command.

Meanwhile, when the cursor moves as illustrated in FIG. 4B, the ultrasound imaging apparatus 100 may perform Haptic functions to enable the user to easily recognize changes in depth. In this regard, Haptic functions refer to tactile feedback recognizable by the user. The ultrasound imaging apparatus according to an embodiment may provide tactile feedback together with the change in UI as illustrated in FIG. 4B.

Figure 4C:
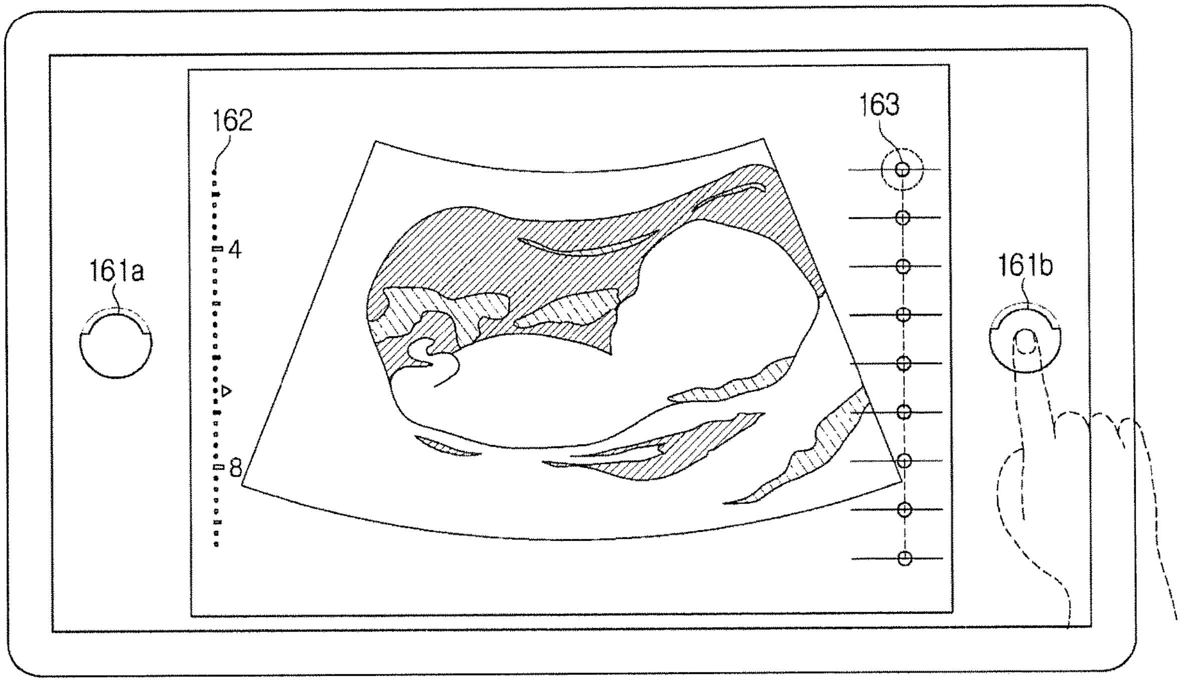
Figure 4D:
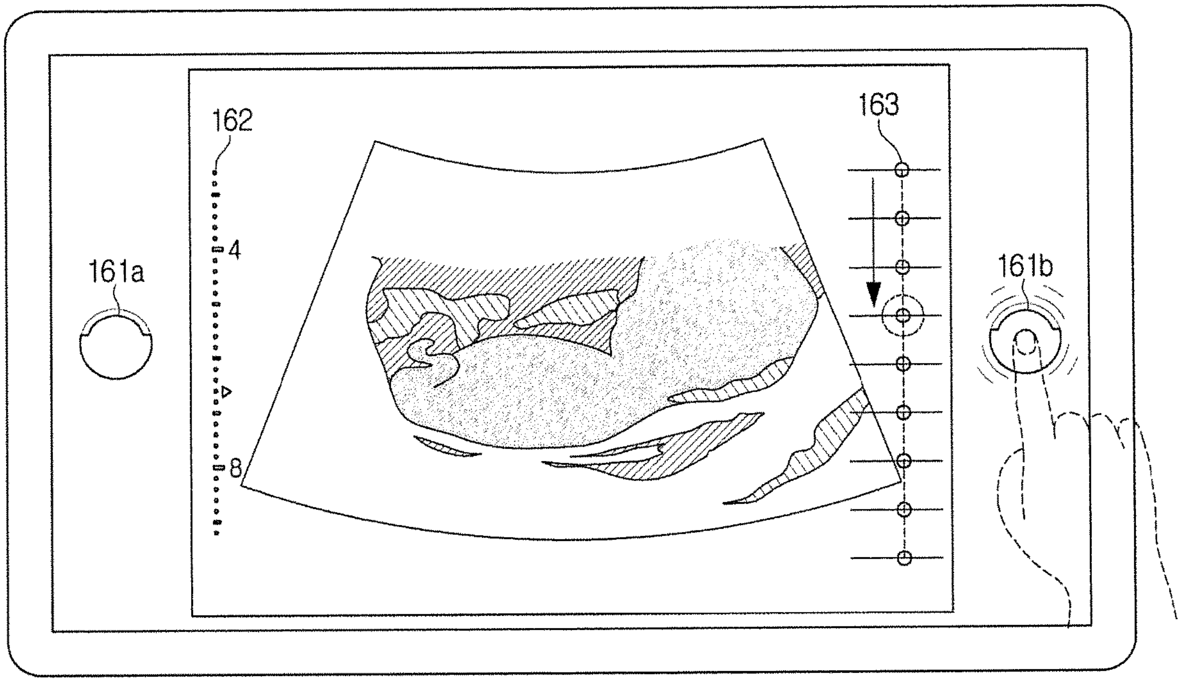

FIGS. 4C and 4D are views for describing operation of controlling TGC by the user.

Referring to FIG. 4C, the user may touch the second button 161*b* using a finger. In this case, the processor 400 may display a cursor at the axis 163 of the second graph indicating gains of a current ultrasound image.

Then, when the user touches the second button 161*b* of the touch screen 152 with pressure, the processor 400 may move the position of the cursor proportionally to the amount of the pressure and touch time.

Meanwhile, according to the embodiment described with reference to FIG. 4C, tactile feedback may also be provided to the user according to movement of the cursor in the same manner as in FIG. 4B.

FIG. 4D illustrates an ultrasound image in which a closer position is set with lower TGC.

In the ultrasound image illustrated in FIG. 4D, a region closer to the ultrasound probe 200 (upper portion of FIG. 4D) is represented as white. Here, a white background indicates that the closer region is represented lighter.

In conclusion, the ultrasound imaging apparatus 100 may control the degree of amplification, i.e., focusing, with respect to depth in the ultrasound image based on the touch pressure or touch time of the user.

Meanwhile, FIGS. 4A to 4D illustrate only examples of the embodiments of the present disclosure. The ultrasound imaging apparatus 100 may display various types of UIs in accordance with touch pressure applied by the user.

Figure 5A:
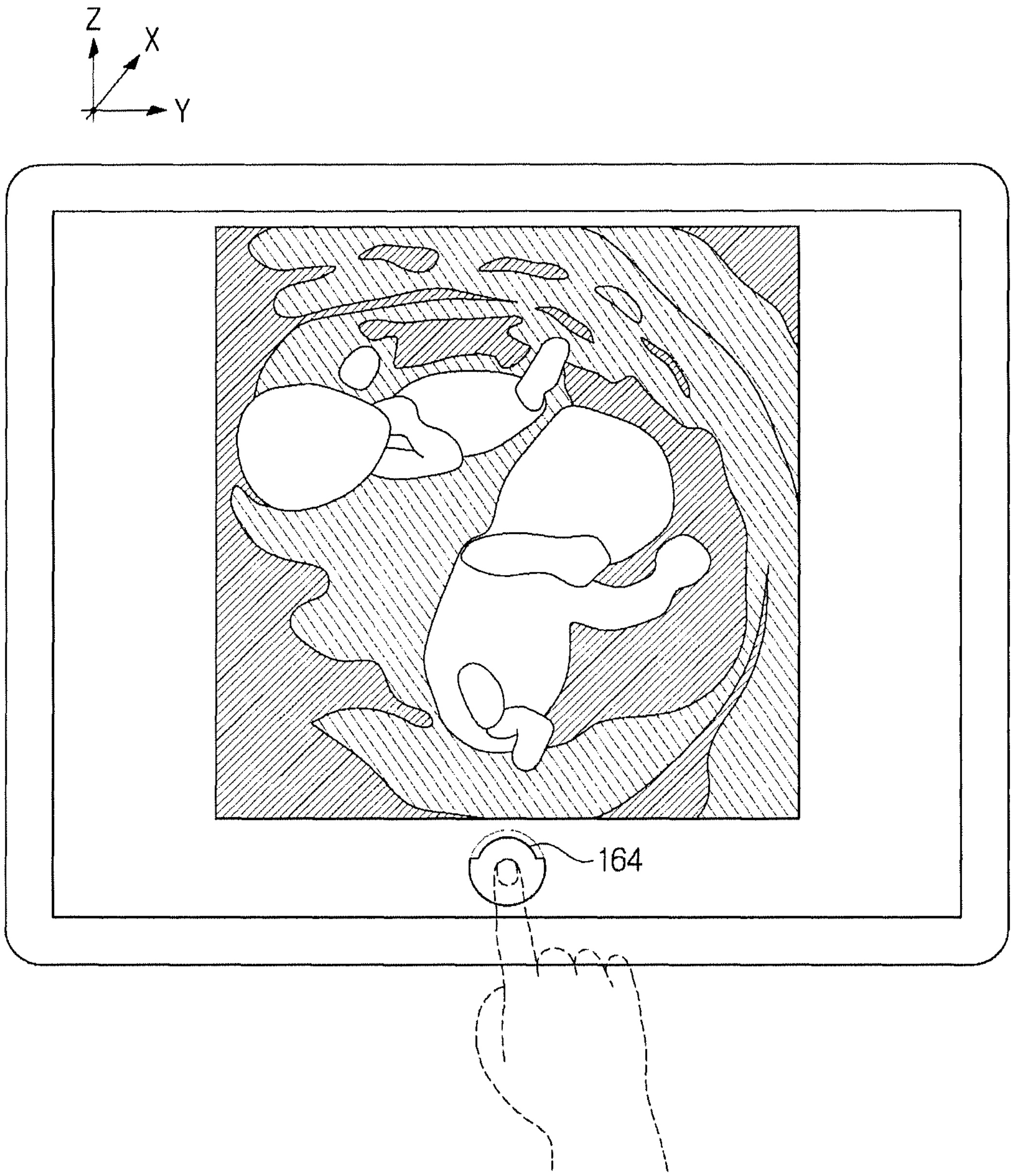
FIGS. 5A to 5C are views for describing another examples of the touch screen changing in accordance with touch pressure or touch time.
Figure 5B:
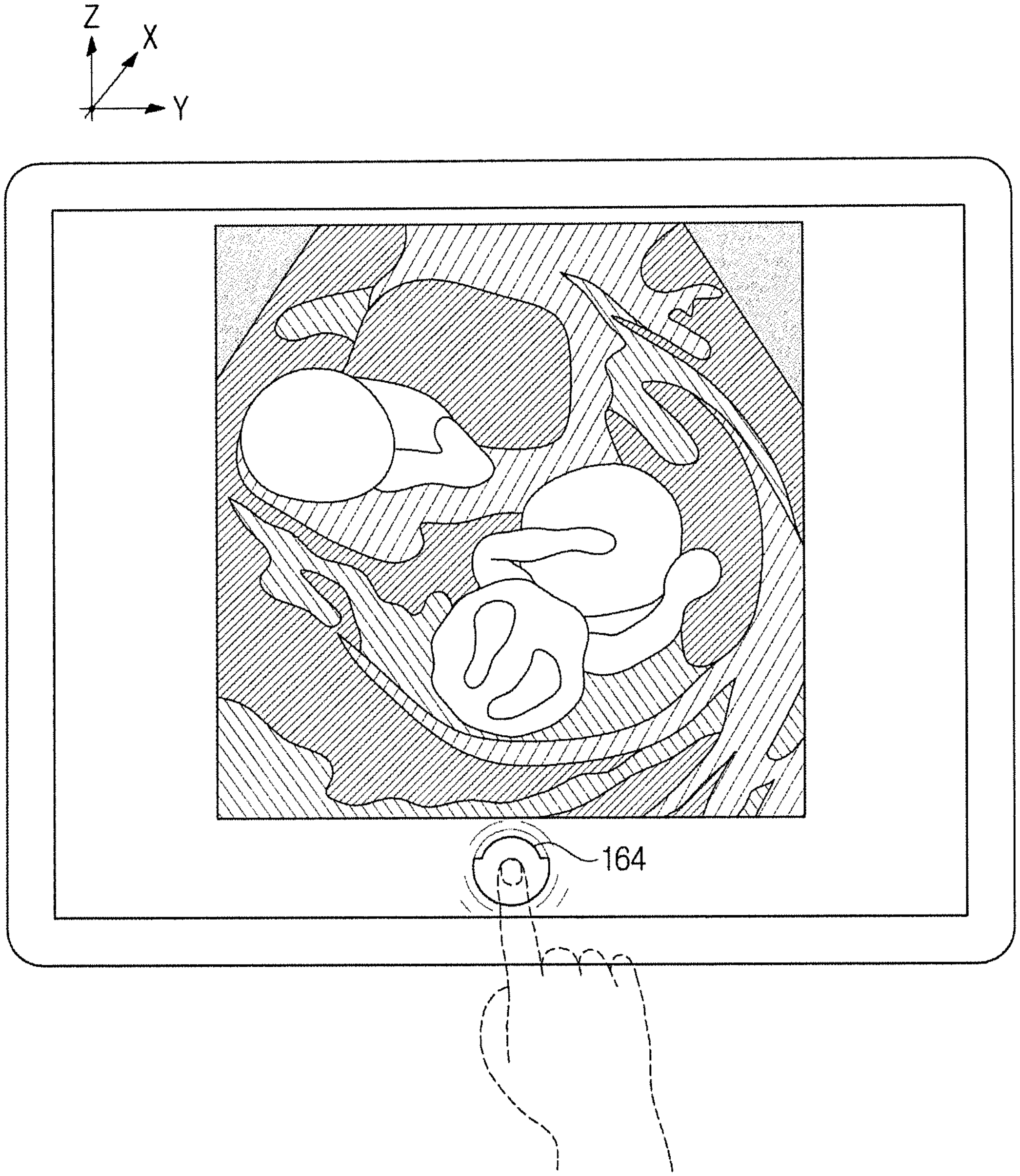
Figure 5C:
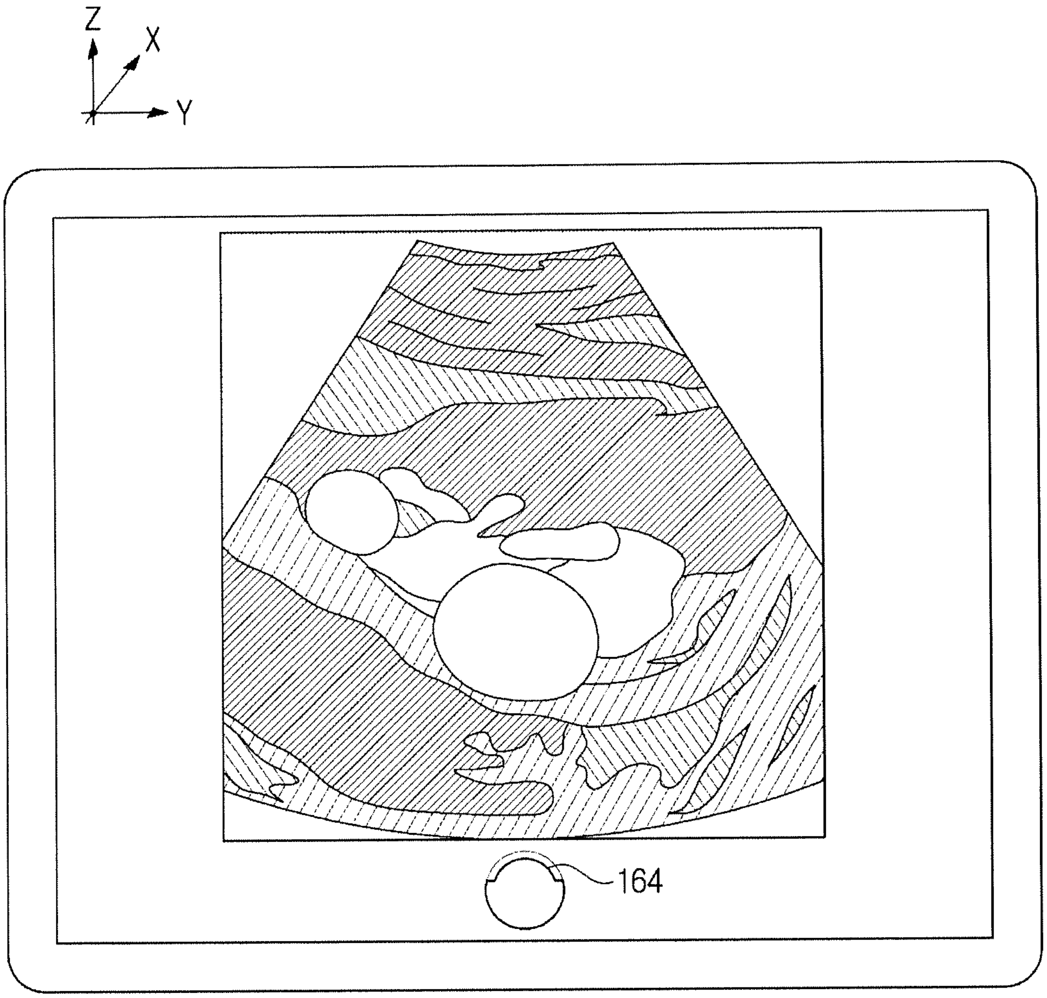

FIGS. 5A to 5C are views for describing another examples of the touch screen changing in accordance with touch pressure or touch time. Hereinafter, the drawings will be synthetically described to avoid repeated descriptions.

FIGS. 5A to 5C schematically illustrate ultrasound images of twin fetuses in a pregnant woman.

The user may control the ultrasound imaging apparatus 100 to rotate an ultrasound image of the twin fetuses to obtain various images thereof. To this end, the user may touch a button-shaped UI displayed on the touch screen 152. Hereinafter, the button-shaped UI will be referred to as a button 164 for descriptive convenience.

Then, the user may apply a pressure to the touched button 164 as illustrated in FIG. 5B, and the processor 400 may control the ultrasound image to rotate by a preset degree proportionally to the amount of the pressure.

FIG. 5B is an ultrasound image acquired by rotating the ultrasound image of FIG. 5A from the Z-axial direction to the X-axial direction. FIG. 5C is an ultrasound image acquired by rotating the ultrasound image of FIG. 5B by a degree desired by the user and detaching the finger from the button 164.

That is, the ultrasound image of FIG. 5C illustrates a state obtained by rotating the ultrasound image of FIG. 5A by 270 degrees from the Z-axial direction to the X-axial direction.

The ultrasound imaging apparatus 100 according to an embodiment enables the user to rotate the ultrasound image using only the touch pressure and identify the object in various angles.

Meanwhile, the ultrasound images illustrated in FIGS. 5A to 5C are only examples of the embodiments of the present disclosure, and the embodiment may include various modifications.

FIGS. 6A to 6E are views for describing operation of removing a region having the same intensity range according to depth. Hereinafter, the drawings will be synthetically described to avoid repeated descriptions.

Figure 6A:
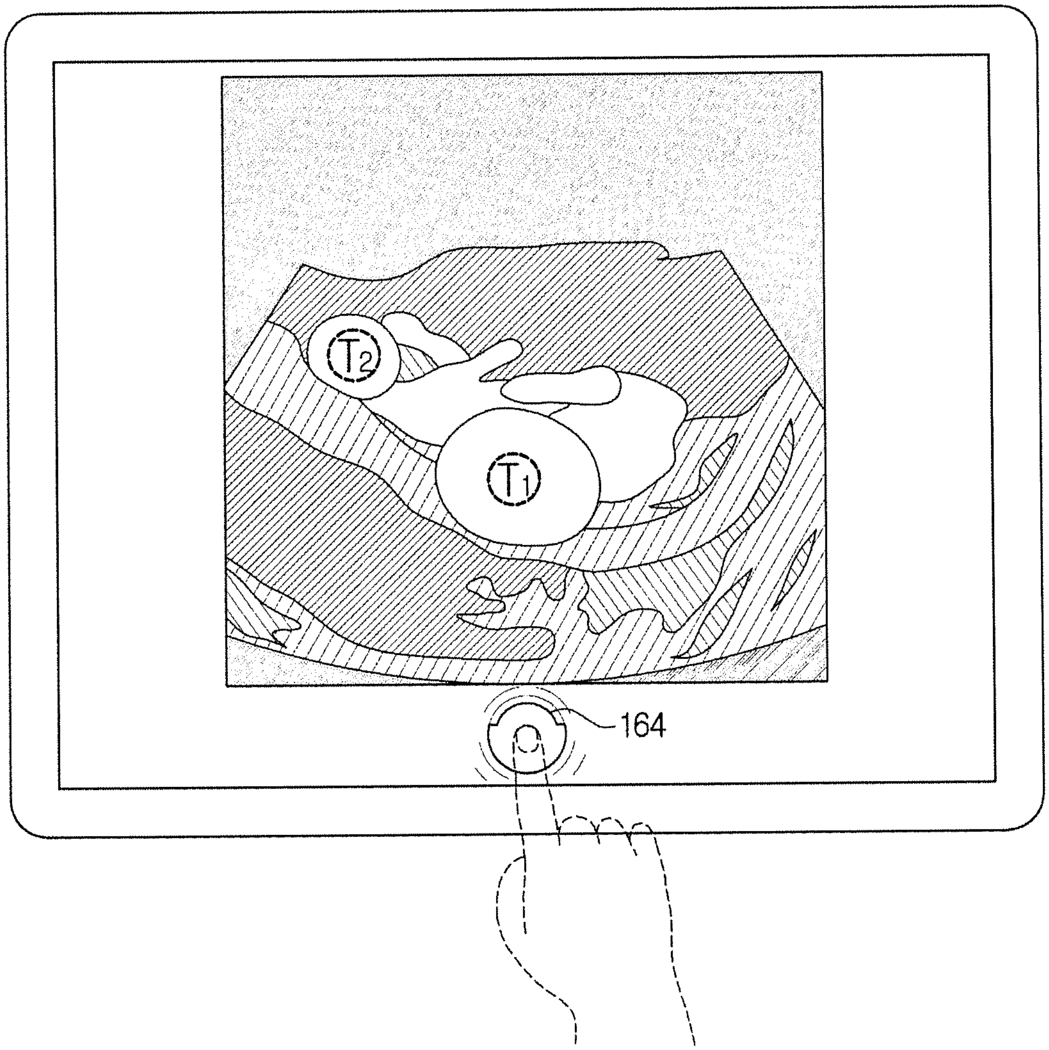
FIGS. 6A to 6E are views for describing operation of removing a region having the same intensity range according to depth.

FIG. 6A illustrates that the user touches the button 164 on the screen illustrated in FIG. 5C again to remove a region having the same intensity range.

As used herein, the term "intensity" refers to energy of ultrasound per unit area while a wave passes through a medium. Thus, the same intensity range refers to a portion of the ultrasound image output with the same brightness due to the same intensity of ultrasound reflected by the object.

Referring back to FIG. 6A, an upper portion of the ultrasound image is darker than that of FIG. 5C. FIG. 6A illustrates that transparency of the region having the same intensity range is adjusted according to depth in the ultrasound image.

Figure 6B:
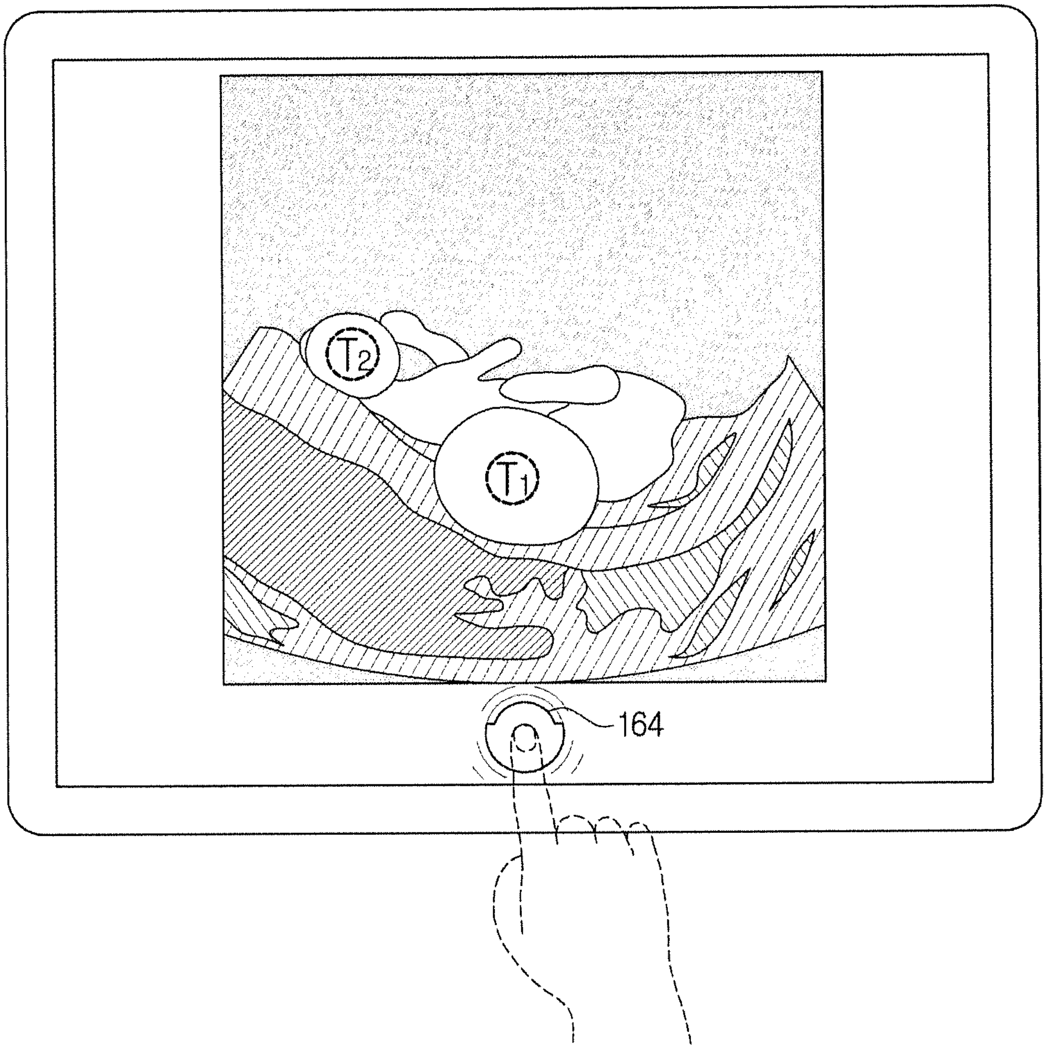
Figure 6C:
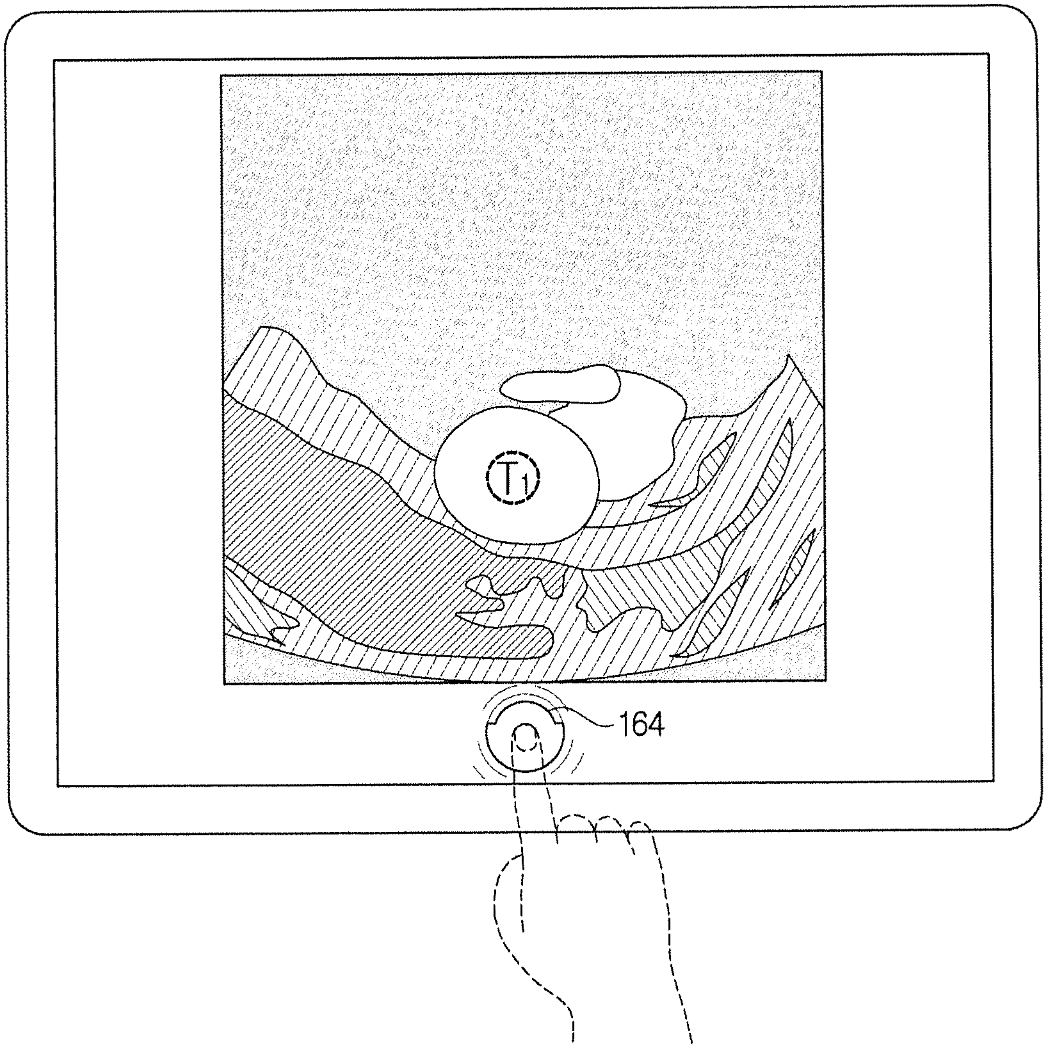
Figure 6D:
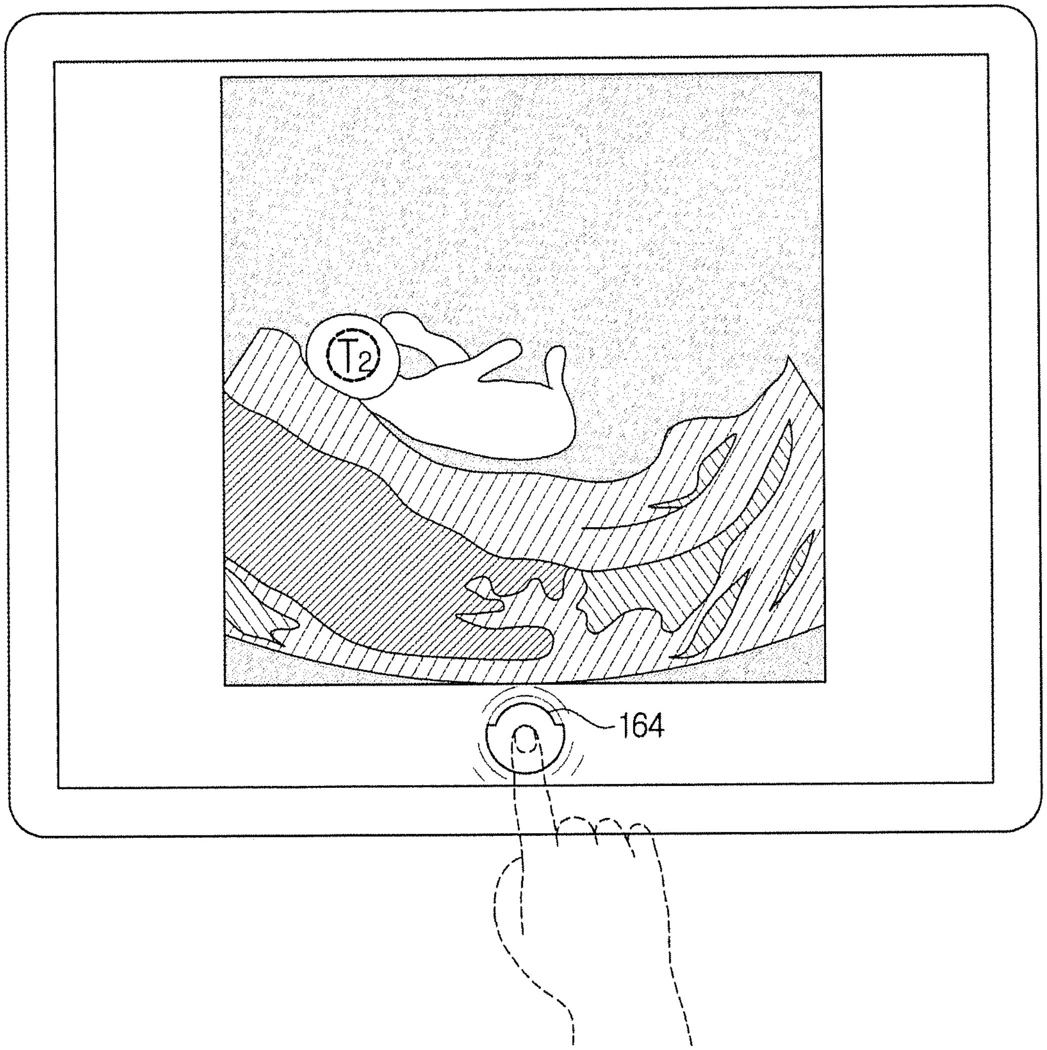

If the user keeps pressing the button 164 for Force Touch after the ultrasound imaging apparatus 100 outputs the ultrasound image of the object as illustrated in FIG. 6A, the ultrasound imaging apparatus 100 may sequentially output images of FIGS. 6B to 6D.

Referring to FIG. 6B, a region having the same intensity range located at a next depth to that adjusted as illustrated in FIG. 6A is adjusted. The ultrasound imaging apparatus 100 according to an embodiment may adjust transparency of the region having the same intensity range located at the next depth at a predetermined duration of time after the user starts applying a pressure to the button 164

FIG. 6C illustrates an ultrasound image output by the ultrasound imaging apparatus 100 according to another embodiment.

In FIG. 6C, a second fetus T2 is removed from the twin fetuses T1 and T2, and only a first fetus T1 is output.

In FIG. 6B, the twin fetuses T1 and T2 may be located at the same depth. However, the intensities of the twin fetuses T1 and T2 may be different from each other. Thus, the ultrasound imaging apparatus 100 may output an image from which the second fetus T2 is removed between the twin fetuses T1 and T2 when the user keeps inputting a pressure to the button 164.

Referring to FIG. 6D, when the user further keeps inputting the pressure to the button 164, the ultrasound imaging apparatus 100 may output the second fetus T2, which was removed in the FIG. 6C, again.

When the user stops to input the touch pressure, the ultrasound imaging apparatus 100 may output only the second fetus T2.

The order of selecting one of the twin fetuses separated according to intensity may be preset in the ultrasound imaging apparatus 100 and changed by the user.

Meanwhile, the ultrasound imaging apparatus 100 according to the embodiment described with reference to FIGS. 6B to 6D may also provide tactile feedback to allow the user to recognize adjustment of transparency or the order of selecting the fetuses as illustrated in FIG. 4B.

Figure 6E:
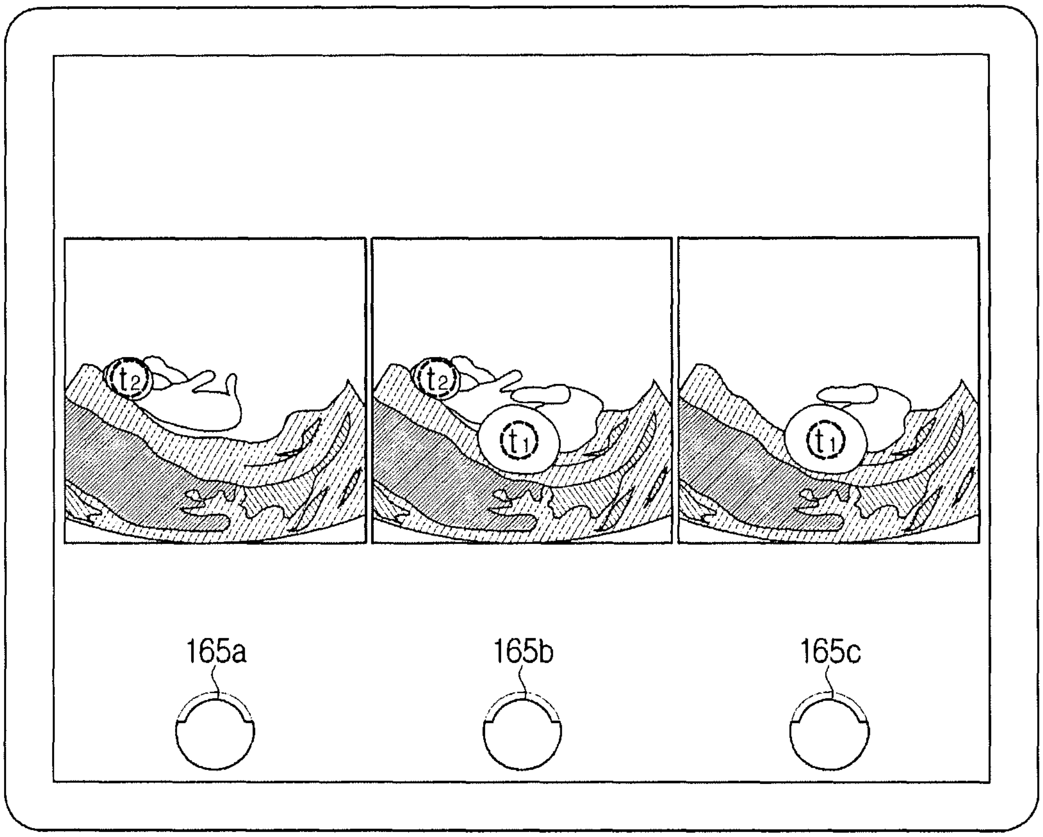

FIG. 6E is a view for describing a method of inducing the user to select one of the twins by the ultrasound imaging apparatus 100.

Although the ultrasound imaging apparatus 100 induces the user to select the fetus while sequentially outputting the images illustrated in FIGS. 6C and 6D, the ultrasound imaging apparatus 100 may also output an image in a preset image mode as illustrated in FIG. 6E in accordance with the touch pressure of the user.

The ultrasound imaging apparatus 100 may display three buttons 165*a*, 165*b*, and 165*c* and images respectively corresponding thereto, and the user may touch a desired image by touching one of the three buttons 165*a*, 165*b*, and 165*c*.

Meanwhile, UI operation in accordance with the touch pressure illustrated in FIGS. 6A to 6E is examples of the embodiments of the present disclosure and may include various other modifications, without being limited thereto.

FIGS. 7A to 7D are views for describing operation of removing a region having the same intensity range according to depth. Hereinafter, the drawings will be synthetically described to avoid repeated descriptions.

FIGS. 7A to 7D schematically illustrate ultrasound images of a placental projection.

Figure 7A:
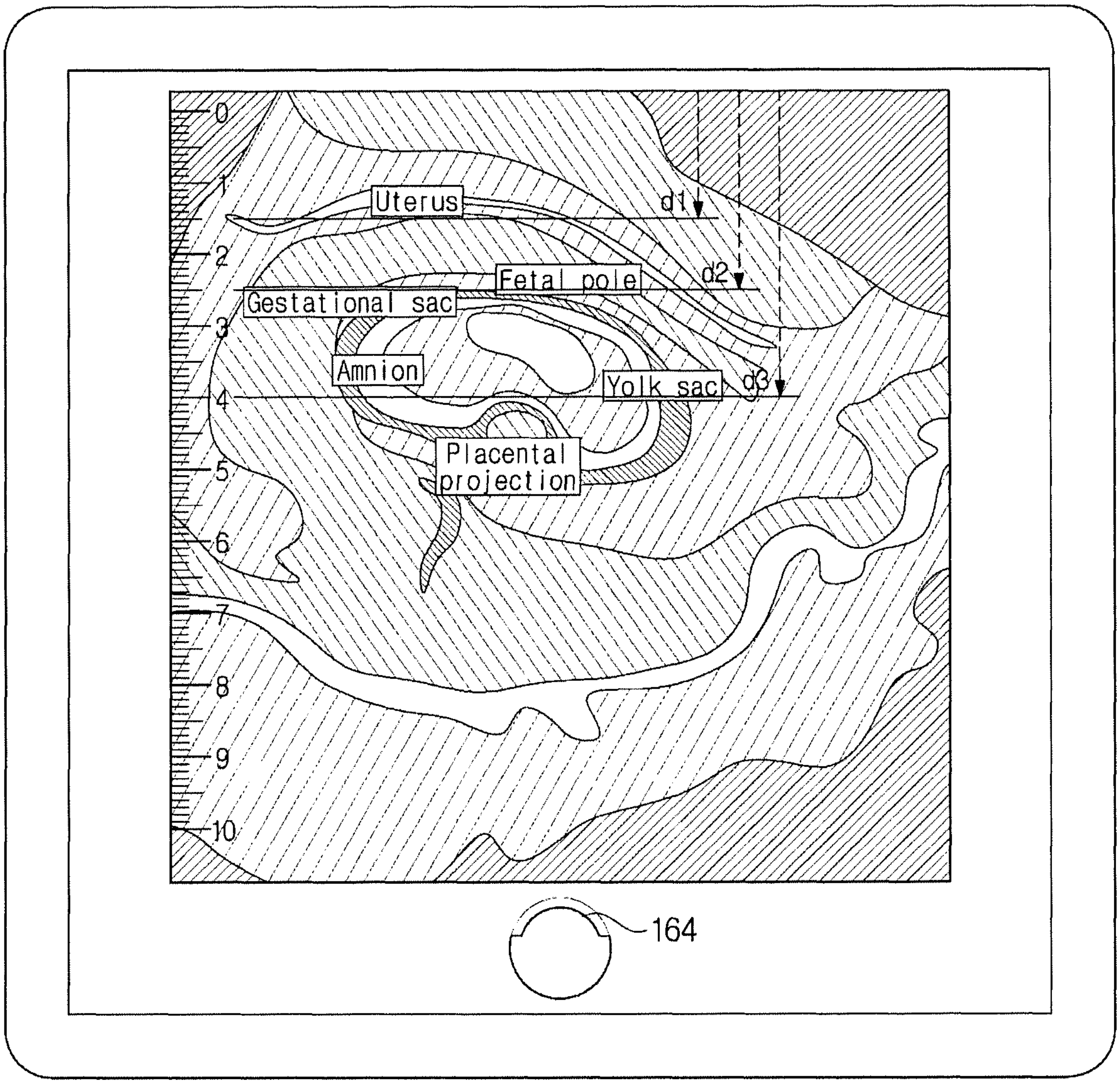
FIGS. 7A to 7D are views for describing operation of removing a region having the same intensity range according to depth.

In FIG. 7A, a depth d1 indicates a point when a uterus starts. A line located at a depth d2 indicates a fetal pool in a gestational sac. The gestational sac is illustrated therebelow, and an amnion is illustrated below the gestational sac. A depth d3 indicates a yolk sac. Hereinafter, these marks are omitted in the following descriptions with reference to FIGS. 7B to 7D.

Figure 7B:
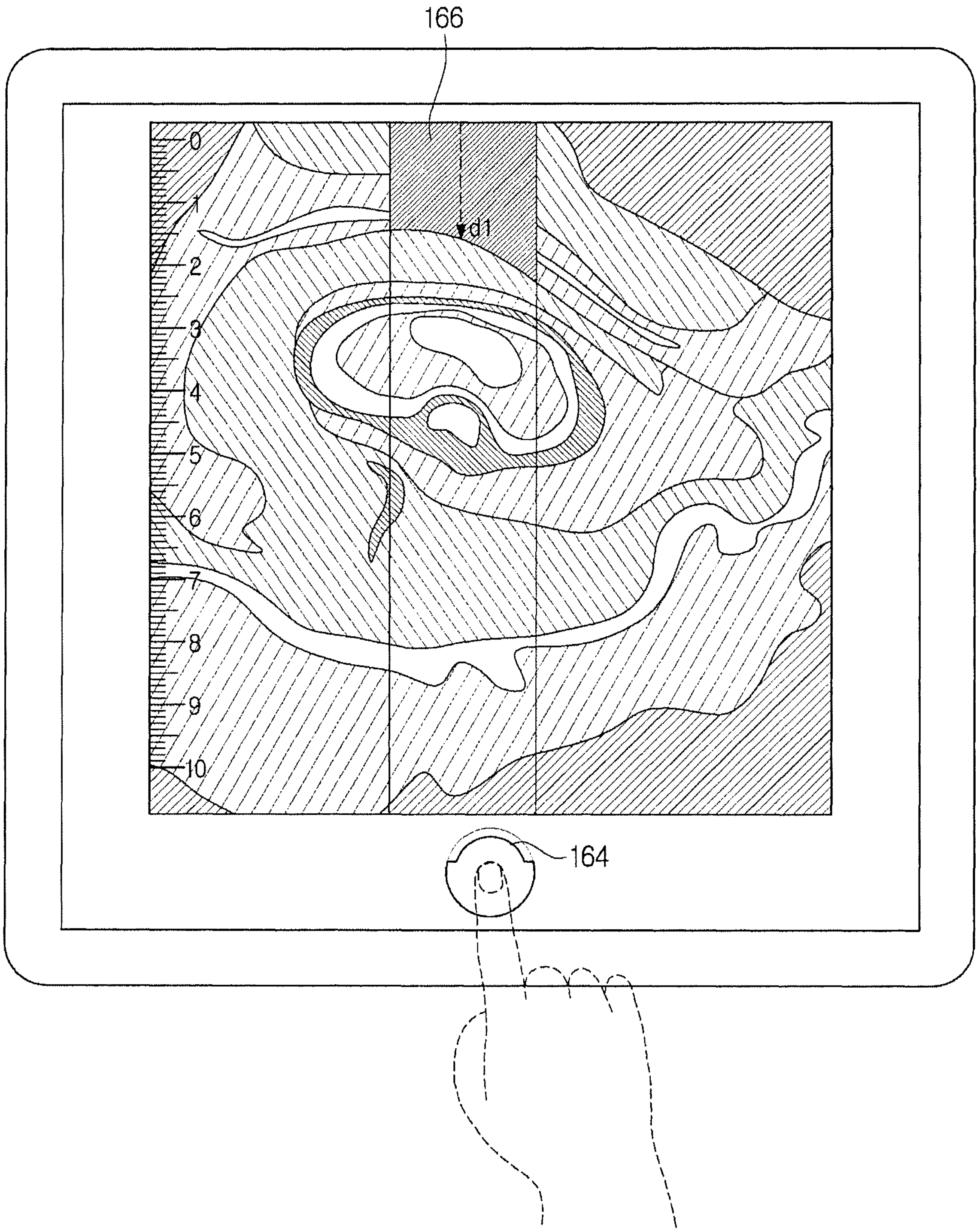

Referring to FIG. 7B, the user touches a button-shaped UI, hereinafter, referred to as button 164. The ultrasound imaging apparatus 100 may emphasize a predetermined region.

In this regard, the predetermined region may be a region in the object to be observed in detail by the user in the generated ultrasound image, i.e., region of interest (ROI) 166. In FIG. 7B, the ROI 166 may be displayed with adjusted brightness and transparency compared with the other regions of the ultrasound image.

That is, according to an embodiment, the ROI 166 may be displayed or transparency thereof may be adjusted proportionally to the touch pressure of the user.

Meanwhile, various methods may be used to display the ROI 166 by the ultrasound imaging apparatus 100, and the ROI 166 may be displayed using various figures and colors, without limitation. Also, stages to display the ROI 166 may also be omitted as illustrated in FIG. 7B.

As described above, the ultrasound imaging apparatus 100 may remove a portion of the placental projection having the same intensity range corresponding to the depth d1 in accordance with a touch pressure or touch time of the user.

Figure 7C:
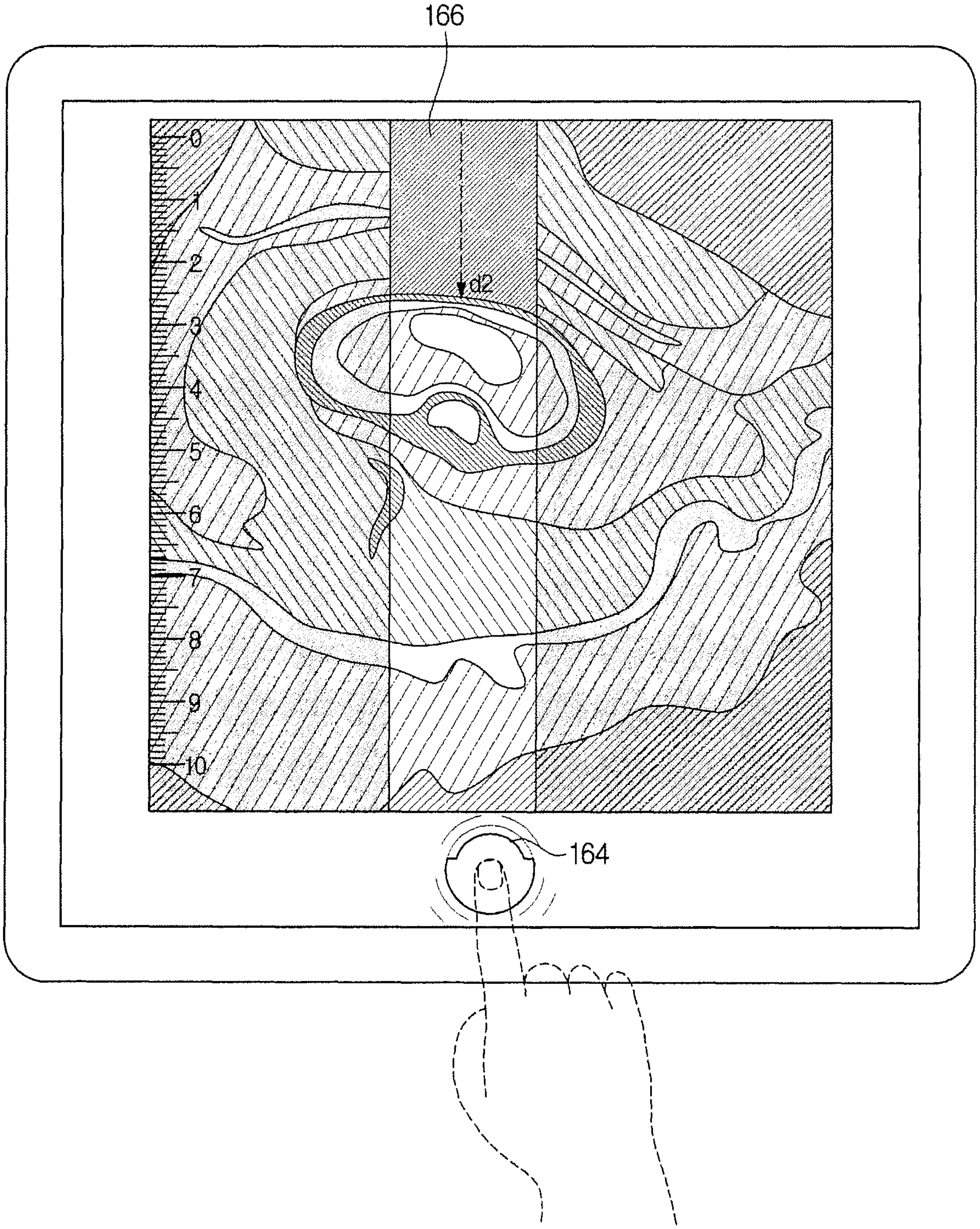

When the user applies a greater pressure to the button 164, the ultrasound imaging apparatus 100 may sequentially remove a region having the same intensity range corresponding to the depth d2 as illustrated in FIG. 7C.

If the user desires to output a detailed image of the yolk sac corresponding to the depth d3, the user may detach the finger from the button 164 at a time when the removing order reaches the depth d3.

Figure 7D:
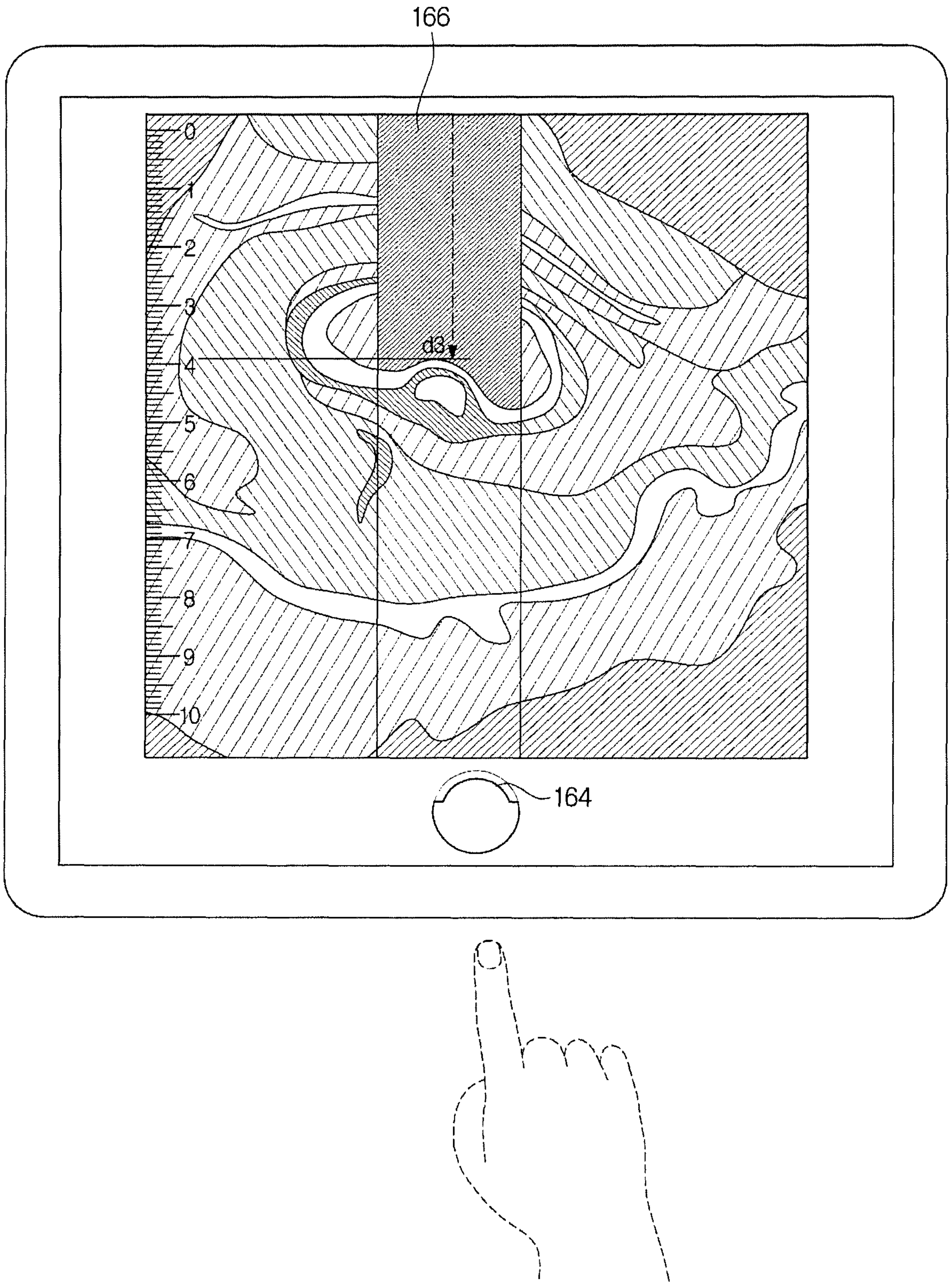

That is, FIG. 7D illustrates an ultrasound image output by the ultrasound imaging apparatus 100 after the user removes the touch pressure.

Meanwhile, the ultrasound imaging apparatus 100 according to the embodiment described with reference to FIGS. 7B to 7D may also additionally provide tactile feedback to allow the user to easily recognize changes in the UI as described above with reference to FIG. 4B.

FIGS. 8A to 8D are views for describing another UI operation according to the present disclosure. Hereinafter, the drawings will be synthetically described to avoid repeated descriptions.

Figure 8A:
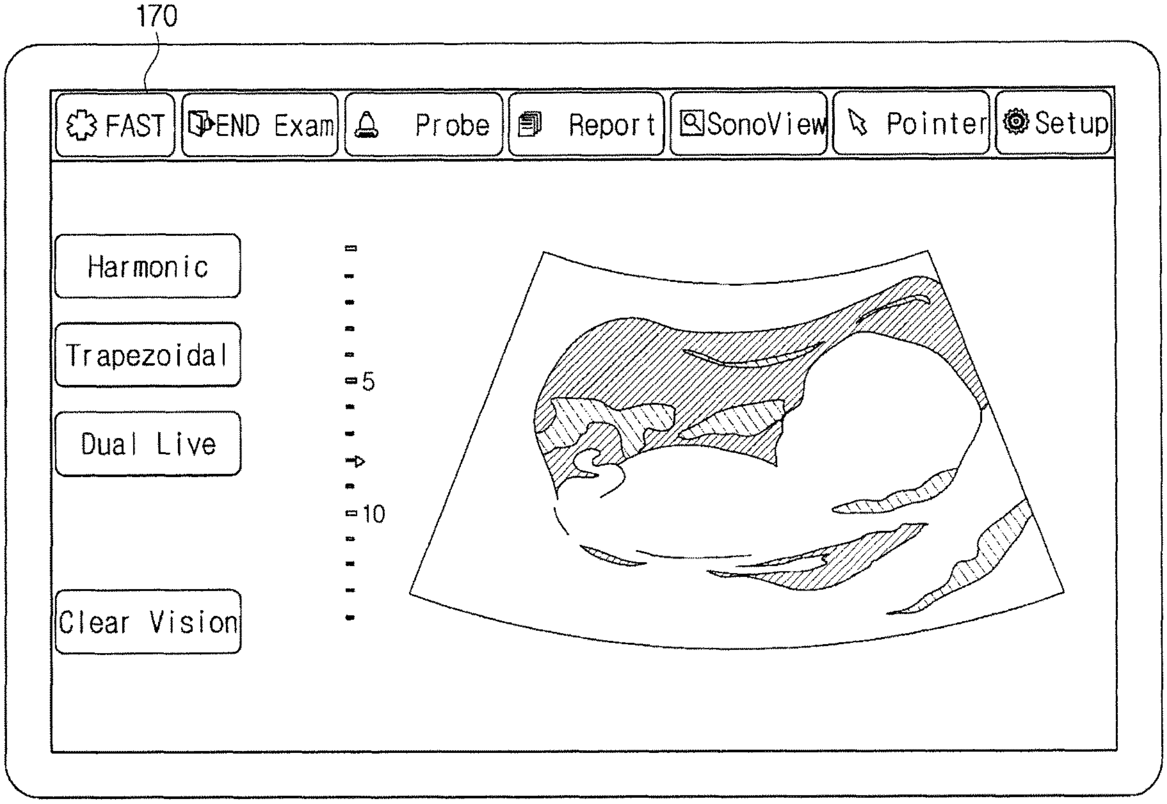
FIGS. 8A to 8D are views for describing another UI operation according to the present disclosure.

FIG. 8A schematically illustrates menu buttons enabling the user to select various UIs and an ultrasound image selected thereby displayed on the touch screen 152.

Particularly, in FIG. 8A, FAST, END EXAM, Probe, Report, SonoView, Pointer, and Setup indicate a main menu selectable in accordance with a touch input or touch time of the user. In addition, Harmonic, Trapezoidal, Daul Live, and ClearVision indicate a sub-menu.

The menus and image illustrated in FIG. 8A are only examples of the touch screen before the user's touch input according to an embodiment, without being limited thereto.

Figure 8B:
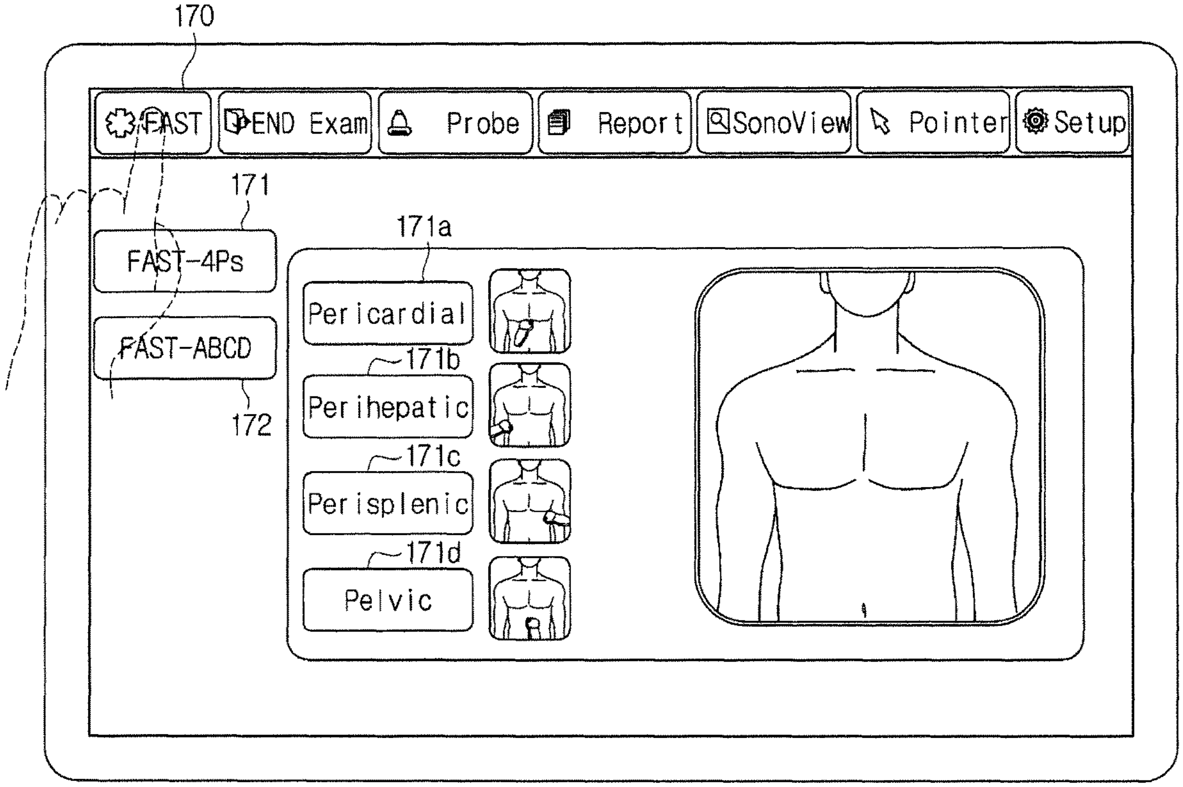

Referring to FIG. 8B, the user may touch a FAST 170 menu on the screen illustrated in FIG. 8A.

Here, the FAST is an abbreviation of Focused Assessment Sonography in Trauma referring to direct ultrasound for external injuries to judge pericardial tamponade or hemoperitoneum.

The sub-menu of the FAST 170 may include FAST-4Ps 171 and FAST-ABCD 172. The FAST-4Ps 171 may further have a sub-menu including Pericardial 171*a*, Perihepatic 171*b*, Perislpenic 171*c*, and Pelvic 171*d*. It may be understood that the names of the sub-menus are related to positions of the object to which ultrasound is transmitted.

If the user touches the FAST 170 menu as illustrated in FIG. 8B, the ultrasound imaging apparatus 100 may convert the screen of FIG. 8A into a screen illustrated in FIG. 8B.

Conventionally, the user touches the sub-menu after moving the finger from the FAST 170 menu or transmits an input signal to the processor 400 using another input unit 153 of the input device 151.

Figure 8C:
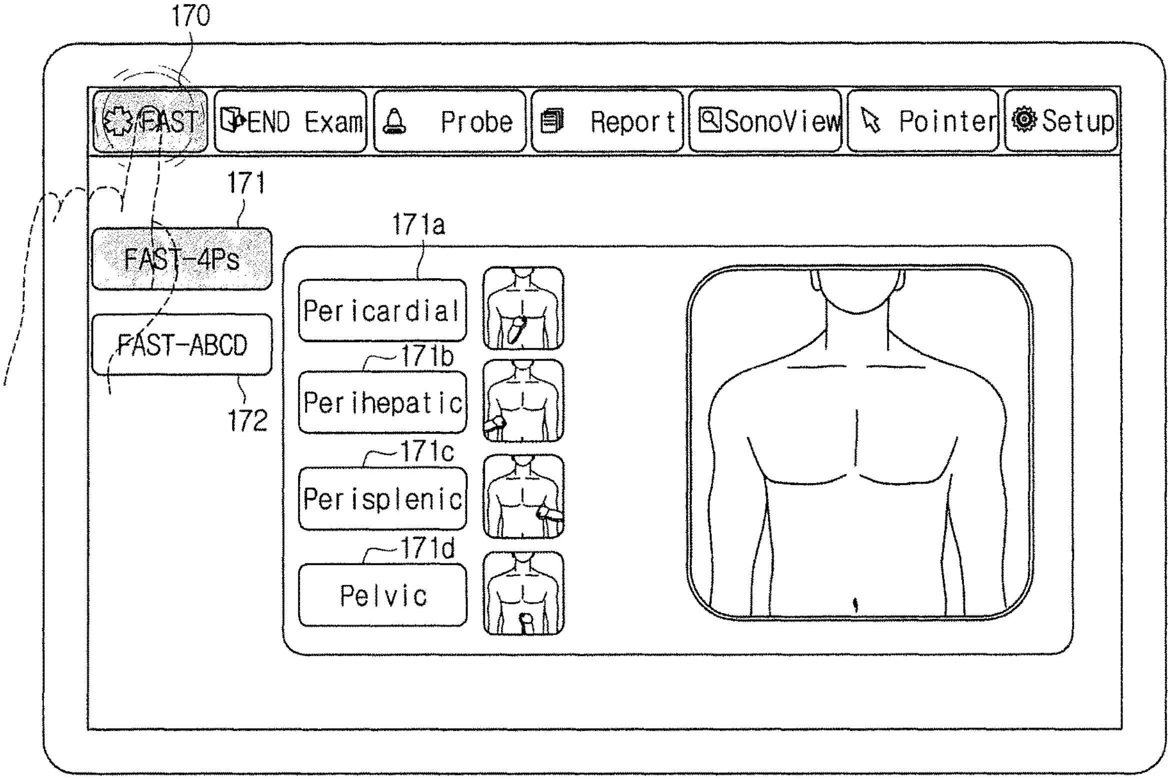

However, in the ultrasound imaging apparatus 100 according to an embodiment, the user may select the sub-menu, i.e., FAST-4Ps 171 and FAST-ABCD 172, by touching and applying a pressure to the FAST 170 menu as illustrated in FIG. 8C.

Figure 8D:
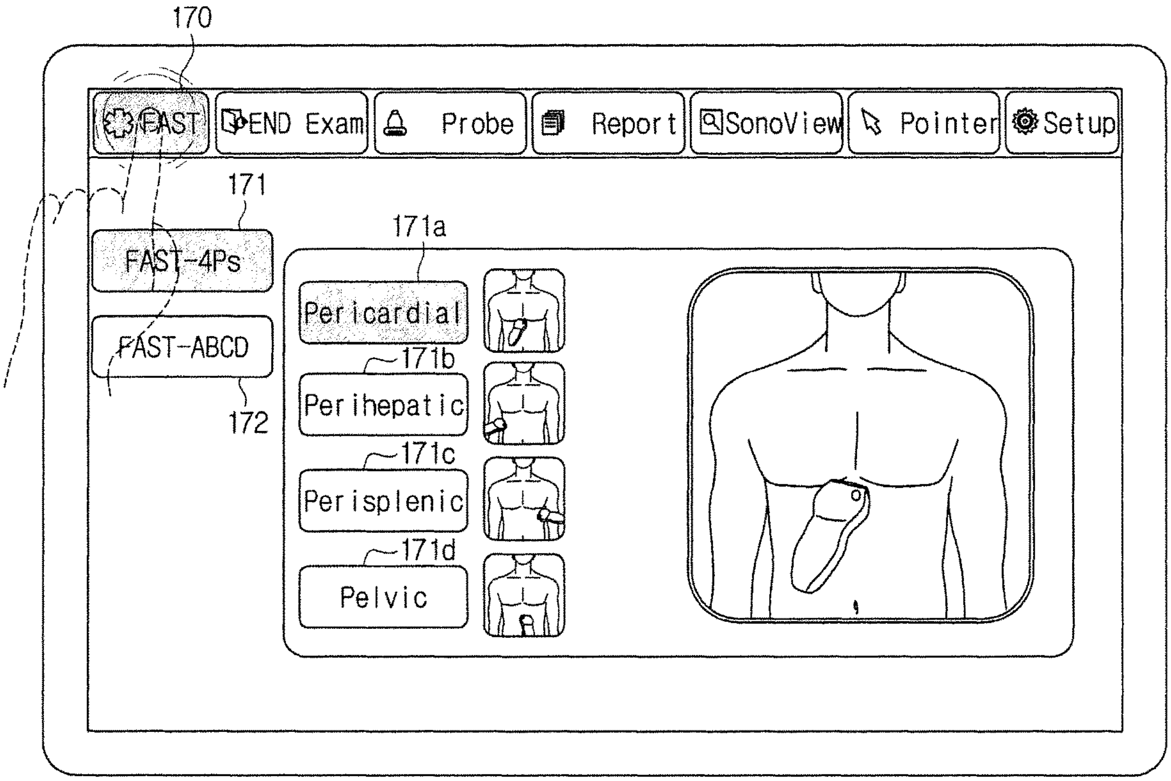

In addition, the ultrasound imaging apparatus 100 may also control the image according to a preset order configured to select one sub-menu of the FAST-4Ps 171, i.e., one of the Pericardial 171*a*, Perihepatic 171*b*, Perislpenic 171*c*, and Pelvic 171*d*, by applying a greater pressure thereto as illustrated in FIG. 8D.

Referring to FIG. 8D, the ultrasound imaging apparatus 100 may output an image in which the probe 200 is located at a region of the Pericardial 171*a* sub-menu, i.e., a pericardial region.

Then, the user may stop Force Touch when the cursor is located at one of the Pericardial 171*a*, Perihepatic 171*b*, Perislpenic 171*c*, and Pelvic 171*d* positions, and the ultrasound imaging apparatus 100 may output an image corresponding to the menu.

Meanwhile, the ultrasound imaging apparatus 100 may provide tactile feedback enabling the user to easily recognize the image simultaneously outputting the image as described above with reference to FIGS. 8B to 8D.

Figure 9:
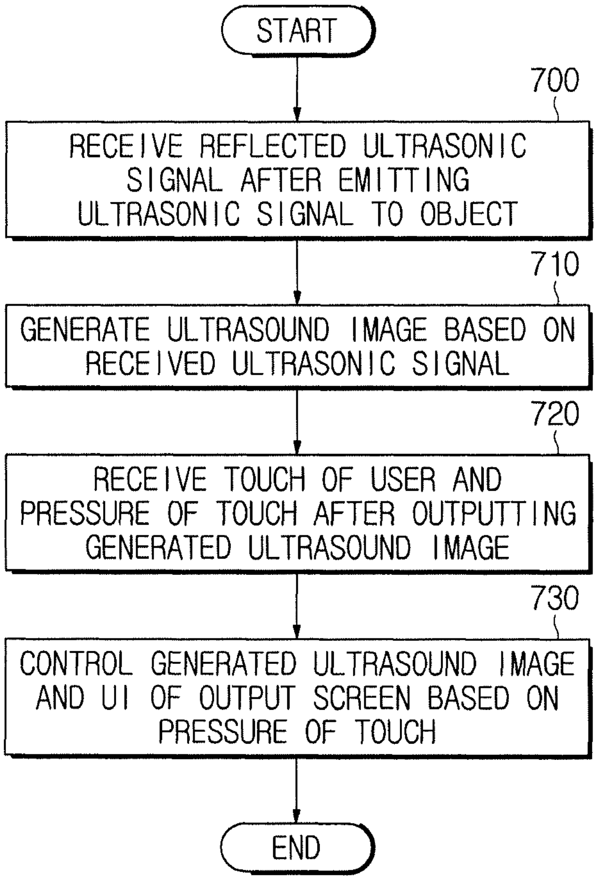
FIG. 9 is a flowchart for describing a method of controlling an ultrasound imaging apparatus according to an embodiment.

FIG. 9 is a flowchart for describing a method of controlling an ultrasound imaging apparatus according to an embodiment.

Referring to FIG. 9, the ultrasound imaging apparatus 100 emits ultrasonic signals to the object using the probe 200 and receives reflected ultrasonic signals (700).

The received ultrasonic signals are transmitted to the processor 400 via the beamforming unit 300, and the processor 400 generates an ultrasound image based on the received ultrasonic signals (710).

The ultrasound image generated by the processor 400 may be output through the touch screen 152 or the display 160. Also, the processor 400 may control the touch screen 152 or the display 160 to output various UIs configured to assist the user to control the ultrasound image, as graphics together with the ultrasound image.

After identifying the output image, the user may touch the touch screen 152. In this case, the ultrasound imaging apparatus 100 may receive not only the position of the user's touch on the touch screen 152, but also a pressure of the touch (720).

As described above, although the touch screen 152 is distinguished from the display 160 in the ultrasound imaging apparatus 100, the touch screen 152 may also be integrated with the display 160 according to another embodiment. The integrated device may output an ultrasound image simultaneously receiving a touch with a pressure.

The pressure may be input via Force Touch or using the touch pen 155 described above with reference to FIGS. 2A and 2B, without being limited thereto.

The processor 400 may control the generated ultrasound image and UIs displayed on the screen in accordance with the amount of pressure input by the user and the touch time (730).

For example, the ultrasound imaging apparatus 100 may select a depth of the generated ultrasound image or remove a region having intensity within a preset range to the depth in accordance with the amount of the pressure and duration of the applied pressure.

That is, the ultrasound imaging apparatus 100 may perform various operations based on the touch pressure applied by the user and assist the user to easily control the ultrasound imaging apparatus.

As is apparent from the above description, the ultrasound imaging apparatus and the method of controlling the same may control the ultrasound image in various ways and improve convenience of the user by controlling the touch screen or the display output by the ultrasound imaging apparatus in accordance with a touch pressure or touch time of the user.

Although a few embodiments of the present disclosure have been shown and described, it would be appreciated by those skilled in the art that changes may be made in these embodiments without departing from the principles and spirit of the disclosure, the scope of which is defined in the claims and their equivalents.

What is claimed is:

1. An ultrasound imaging apparatus comprising:

a probe configured to emit an ultrasonic signal to an object and receive a reflected ultrasonic signal;

a touch screen configured to output an ultrasound image and a user interface (UI) button along with the ultrasound image and receive a first touch and second touch having different pressure intensities; and a processor configured to generate the ultrasound image based on the ultrasonic signal received by the probe and to control the ultrasound image based on a pressure intensity of the first touch and a pressure intensity of the second touch received by the UI button, wherein the processor removes a portion of the ultrasound image of a first object located at a first depth based on the pressure intensity of the first touch, and sequentially removes another portion of the ultrasound image of a second object within a second depth based on the pressure intensity of the second touch, and the second pressure is greater than the first pressure, and the second depth is deeper than the first depth.

2. The ultrasound imaging apparatus according to claim 1, wherein the processor controls a TGC (Time Gain Compensation) of the ultrasound image corresponding to a selected depth based on a difference of pressure of the second touch.

3. The ultrasound imaging apparatus according to claim 1, wherein the processor controls transparency of a region of the image having a predetermined intensity range based on a selected depth and a difference of pressure of the second touch.

4. The ultrasound imaging apparatus according to claim 1, wherein the processor controls focusing of the ultrasound image based on a difference of pressure of the second touch.

5. The ultrasound imaging apparatus according to claim 1, wherein the processor controls a region of interest in the ultrasound image based on a difference of pressure of the second touch.

6. The ultrasound imaging apparatus according to claim 1, wherein the processor controls the ultrasound image to rotate based on a difference of pressure of the second touch.

7. The ultrasound imaging apparatus according to claim 1, wherein the processor controls a menu displayed on the touch screen based on a difference of pressure of the second touch.

8. The ultrasound imaging apparatus according to claim 1, wherein the touch screen receives a difference of pressure of the first touch and the second touch via a touch pen.

9. The ultrasound imaging apparatus according to claim 1, wherein the processor controls the ultrasound image and the touch screen based on a preset time period during which the pressure is input.

10. A method of controlling an ultrasound imaging apparatus, the method comprising:

emitting an ultrasonic signal to an object and receiving a reflected ultrasonic signal;

generating an ultrasound image based on the received ultrasonic signal and outputting a user interface (UI) button along with the ultrasound image;

receiving a first touch and a second touch having different pressure intensities after outputting the generated ultrasound image; and controlling the ultrasound image based on a pressure intensity of the first touch and a pressure intensity of the second touch, wherein the controlling comprises removing a portion of the ultrasound image of a first object located at a first depth based on the pressure intensity of the first touch received by the UI button, and sequentially removing another portion of the ultrasound image of a second object within a second depth based on the pressure intensity of the second touch received by the UI button, and the second pressure is greater than the first pressure, and the second depth is deeper than the first depth.

11. The method according to claim 10, wherein the controlling further comprises controlling a TGC (Time Gain Compensation) of the ultrasound image corresponding to a selected depth based on a difference of pressure of the second touch.

12. The method according to claim 10, wherein the controlling further comprises controlling transparency of a region of the ultrasound image having a predetermined intensity range based on a selected depth and a difference of pressure of the second touch.

13. The method according to claim 10, wherein the controlling further comprises controlling focusing of the ultrasound image based on a difference of pressure of the second touch.

14. The method according to claim 10, wherein the controlling further comprises controlling a region of interest in the ultrasound image based on a difference of pressure of the second touch.

15. The method according to claim 10, wherein the controlling further comprises controlling the ultrasound image to rotate based on a difference of pressure of the second touch.

16. The method according to claim 10, wherein the controlling further comprises controlling a menu displayed on the touch screen based on a difference of pressure of the second touch.

17. The method according to claim 10, wherein the receiving comprises receiving a difference of pressure of the first touch and the second touch via a touch pen.

18. The method according to claim 10, wherein the controlling comprises controlling the ultrasound image based on a preset time period during which the pressure is input.

* * * * *